US011850058B2

(12) United States Patent
Ford et al.

(10) Patent No.: US 11,850,058 B2
(45) Date of Patent: *Dec. 26, 2023

(54) METHODS AND MAGNETIC IMAGING DEVICES TO INVENTORY HUMAN BRAIN CORTICAL FUNCTION

(71) Applicant: Brain F.I.T. Imaging, LLC, Unadilla, NY (US)

(72) Inventors: John P. Ford, Unadilla, NY (US); Gustavo P. Sudre, Washington, DC (US)

(73) Assignee: Brain F.I.T. Imaging, LLC, Unadilla, NY (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/919,094

(22) Filed: Jul. 1, 2020

(65) Prior Publication Data

US 2020/0330024 A1  Oct. 22, 2020

Related U.S. Application Data

(63) Continuation of application No. 15/472,130, filed on Mar. 28, 2017, now Pat. No. 10,736,557.
(Continued)

(51) Int. Cl.
  *A61B 5/00* (2006.01)
  *A61B 5/055* (2006.01)
  (Continued)

(52) U.S. Cl.
  CPC .......... *A61B 5/4088* (2013.01); *A61B 5/0042* (2013.01); *A61B 5/055* (2013.01);
  (Continued)

(58) Field of Classification Search
  CPC ..... A61B 5/4088; A61B 5/0042; A61B 5/055; A61B 5/246; A61B 5/6803; A61B 5/7203;
  (Continued)

(56) References Cited

U.S. PATENT DOCUMENTS 3,445,760 A   5/1969  Zimmerman
3,506,913 A   4/1970  Lambe et al.
(Continued)

FOREIGN PATENT DOCUMENTS

CN   101583308 A   11/2009
CN   101912255 A   12/2010
(Continued)

OTHER PUBLICATIONS

Cheour, M. et al., "Magnetoencephalography is feasible for infant assessment of auditory discrimination," Sep. 15, 2004, Experimental Neurology, 190, S44-S51.
(Continued)

*Primary Examiner* — Sanjay Cattungal
(74) *Attorney, Agent, or Firm* — Fenwick & West LLC

(57) ABSTRACT

Techniques are described for determining cognitive impairment, an example of which includes accessing a set of epochs of magnetoencephalography (MEG) data of responses of a brain of a test patient to a plurality of auditory stimulus events; processing the set of epochs to identify parameter values one or more of which is based on information from the individual epochs without averaging or otherwise collapsing the epoch data. The parameter values are input into a model that is trained based on the parameters to determine whether the test patient is cognitively impaired.

20 Claims, 17 Drawing Sheets

Related U.S. Application Data

(60) Provisional application No. 62/315,376, filed on Mar. 30, 2016.

(51) Int. Cl.
    *A61B 5/246*     (2021.01)
    *A61B 5/16*      (2006.01)

(52) U.S. Cl.
    CPC ............ *A61B 5/246* (2021.01); *A61B 5/6803* (2013.01); *A61B 5/7203* (2013.01); *A61B 5/7257* (2013.01); *A61B 5/7264* (2013.01); *A61B 5/7267* (2013.01); *A61B 5/162* (2013.01); *A61B 2503/40* (2013.01); *A61B 2560/0223* (2013.01); *A61B 2562/0223* (2013.01); *A61B 2576/026* (2013.01)

(58) Field of Classification Search
    CPC ... A61B 5/7257; A61B 5/7264; A61B 5/7267; A61B 5/162; A61B 2503/40; A61B 2560/0223; A61B 2562/0223; A61B 2576/026; G16H 30/40; G16H 50/70; G16H 50/20; A61P 25/28
    See application file for complete search history.

(56) References Cited

U.S. PATENT DOCUMENTS

| | | | |
|---|---|---|---|
| 3,676,718 | A | 7/1972 | Anderson et al. |
| 3,689,780 | A | 9/1972 | Meissner et al. |
| 3,936,677 | A | 2/1976 | Fulton et al. |
| 4,736,751 | A | 4/1988 | Gevins et al. |
| 4,862,359 | A | 8/1989 | Trivedi et al. |
| 5,325,862 | A | 7/1994 | Lewis et al. |
| 5,326,764 | A | 7/1994 | Milstone et al. |
| 5,381,791 | A | 1/1995 | Qian |
| 5,713,354 | A | 2/1998 | Warden |
| 5,752,514 | A | 5/1998 | Okamura et al. |
| 6,192,276 | B1 | 2/2001 | Strandberg |
| 6,195,576 | B1 | 2/2001 | John |
| 6,230,037 | B1 | 5/2001 | Tsukada et al. |
| 6,256,531 | B1 | 7/2001 | Ilmoniemi et al. |
| 6,471,960 | B1 | 10/2002 | Anderson |
| 6,473,518 | B1 | 10/2002 | Machida et al. |
| 6,665,553 | B2 | 12/2003 | Kandori et al. |
| 6,724,188 | B2 | 4/2004 | Butters et al. |
| 6,745,063 | B2 | 6/2004 | Tsukada et al. |
| 6,784,663 | B2 | 8/2004 | Sarwinski et al. |
| 6,979,688 | B2 | 12/2005 | Ford |
| 6,995,165 | B2 | 2/2006 | Ford |
| 7,002,341 | B2 | 2/2006 | Baudenbacher et al. |
| 7,130,675 | B2 | 10/2006 | Ewing et al. |
| 7,197,352 | B2 | 3/2007 | Gott et al. |
| 7,368,456 | B2 | 5/2008 | Ford |
| 7,662,829 | B2 | 2/2010 | Ford |
| 7,812,030 | B2 | 10/2010 | Ford |
| 7,816,366 | B2 | 10/2010 | Ford |
| 8,030,710 | B2 | 10/2011 | Pidin |
| 8,258,147 | B2 | 9/2012 | Ford |
| 8,489,544 | B2 | 7/2013 | Ford |
| 8,653,090 | B2 | 2/2014 | Ford |
| 9,084,788 | B2 | 7/2015 | Ford |
| 9,095,266 | B1 | 8/2015 | Fu |
| 9,119,855 | B2 | 9/2015 | Ford |
| 9,286,443 | B2 | 3/2016 | Ford et al. |
| 10,588,576 | B2 | 3/2020 | Phillips et al. |
| 10,736,557 | B2 | 8/2020 | Ford et al. |
| 11,337,631 | B2 | 5/2022 | Ford et al. |
| 2002/0115927 | A1 | 8/2002 | Tsukada et al. |
| 2002/0175693 | A1 | 11/2002 | Starr et al. |
| 2003/0042898 | A1 | 3/2003 | Sarwinski et al. |
| 2003/0100844 | A1 | 5/2003 | Miller et al. |
| 2003/0158128 | A1 | 8/2003 | Ford |
| 2004/0002645 | A1 | 1/2004 | Ewing et al. |
| 2004/0145366 | A1 | 7/2004 | Baudenbacher et al. |
| 2004/0171960 | A1 | 9/2004 | Musha et al. |
| 2004/0254443 | A1 | 12/2004 | Gott et al. |
| 2005/0124863 | A1 | 6/2005 | Cook |
| 2005/0215514 | A1 | 9/2005 | Ford |
| 2007/0015728 | A1 | 1/2007 | Ford |
| 2007/0032737 | A1 | 2/2007 | Causevic et al. |
| 2007/0038067 | A1 | 2/2007 | Kandori et al. |
| 2008/0249430 | A1 | 10/2008 | John |
| 2009/0018431 | A1 | 1/2009 | Feiweier et al. |
| 2009/0062676 | A1 | 3/2009 | Kruglikov et al. |
| 2009/0232884 | A1 | 9/2009 | Ford |
| 2010/0203140 | A1 | 8/2010 | Ford |
| 2010/0280334 | A1 | 11/2010 | Carlson et al. |
| 2011/0077260 | A1 | 3/2011 | Ford |
| 2011/0190621 | A1 | 8/2011 | Verdoorn et al. |
| 2012/0084919 | A1 | 4/2012 | McCroskey et al. |
| 2012/0271148 | A1 | 10/2012 | Nelson |
| 2013/0041590 | A1 | 9/2013 | Burich |
| 2013/0245422 | A1 | 9/2013 | D'Arcy et al. |
| 2014/0000630 | A1 | 1/2014 | Ford |
| 2014/0081347 | A1 | 3/2014 | Nelson et al. |
| 2015/0313901 | A1 | 11/2015 | Ford |
| 2016/0045128 | A1 | 2/2016 | Sitt et al. |
| 2016/0081577 | A1 | 3/2016 | Sridhar |
| 2016/0157742 | A1 | 6/2016 | Huang et al. |
| 2017/0224241 | A1 | 8/2017 | Chen |
| 2017/0281071 | A1 | 10/2017 | Ford et al. |
| 2020/0164201 | A1 | 5/2020 | Berenyi et al. |
| 2020/0321124 | A1 | 10/2020 | Ford et al. |

FOREIGN PATENT DOCUMENTS

| | | |
|---|---|---|
| CN | 105852885 A | 8/2016 |
| EP | 1447045 A1 | 8/2004 |
| EP | 1948014 B1 | 12/2017 |
| JP | 2015-527111 A | 9/2015 |
| WO | WO 2005/039585 A1 | 5/2005 |
| WO | WO 2007/008858 A2 | 1/2007 |
| WO | WO 2009/149246 A1 | 12/2009 |
| WO | WO 2013/155385 A1 | 10/2013 |
| WO | WO 2014/004365 A2 | 1/2014 |
| WO | WO 2017/172961 A1 | 5/2017 |
| WO | WO 2018/163178 A1 | 9/2018 |
| WO | WO 2019/070895 A1 | 4/2019 |

OTHER PUBLICATIONS

Bagić et al., "Clinical Magnetoencephalography Practice in the United States Ten Years Later: A Survey-Based Reappraisal," Journal of Clinical Neurophysiology, Nov. 2020, vol. 37, Issue 6, pp. 592-598.

Kligfield et al., "Recommendations for the Standardization and Interpretation of the Electrocardiogram: Part 1: The Electrocardiogram and Its Technology: A Scientific Statement From the American Heart Association Electrocardiography and Arrhythmias Committee, Council on Clinical Cardiology; the American College of Cardiology Foundation; and the Heart Rhythm Society Endorsed by the International Society for Computerized Electrocardiology," Circulation, vol. 115, Issue 10, Mar. 13, 2007, pp. 1306-1324.

"Xeloda (Capecitabine) Tablets Product Label Insert," Roche Pharmaceuticals, 2003, 47 pages.

Bardy, F. et al., "Deconvolution of magnetic acoustic change complex (mACC)," Clinical Neurophysiology, vol. 125, No. 11, 2014, pp. 2220-2231.

Barrows, parts of "Antineoplastic and Immunoactive Drugs," Chapter 86 in Remington: The Science and Practice of Pharmacy, 20th Edition, Gennaro et al. (eds.), Lippincott, Williams & Wilkins, Baltimore, MD, 2000, only pp. 1498 and 1815 supplied.

Beers et al. (eds.), Chapter 126 ("Malignant Tumors") in The Merck Manual of Diagnosis and Therapy, 17th Edition, Merck & Co., Inc., Rahway, NJ, Jan. 1999, only title pages and text pp. 842-843 supplied.

Berendse, H.W. et al., "Magnetoencephalographic Analysis of Cortical Activity in Alzheimer's Disease: a Pilot Study", Clinical Neurophysiology, 2000, pp. 604-612, vol. 111.

(56) References Cited

OTHER PUBLICATIONS

Bland J.M. et al., "Statistical Methods for Assessing Agreement Between Two Methods of Clinical Measurement," Lancet, 1986, pp. 307-310, vol. 327, No. 8476.

Boly, M. et al., "Preserved Feedforward but Impaired Top-Down Processes in the Vegetative State", Science, May 13, 2011, pp. 858-862, vol. 332.

Borg, X., "The Inverse Cube Law for Dipoles," The General Science Journal, Jan. 25, 2009, 2 pages, May be Retrieved at <URL:http://blazelabs.com/inversecubelaw.pdf>.

Cao et al., "5-Fluorouracil Prodrug: Role of Anabolic and Catabolic Pathway Modulation in Therapy of Colorectal Cancer," Clinical Cancer Research, 1995, pp. 839-845, vol. 1, No. 8.

Childress, J. et al., "Cutaneous Hand and Foot Toxicity Associated with Cancer Chemotherapy," American Journal of Clinical Oncology, vol. 26(5), pp. 435-436, 2003.

Chua, D. et al., "Efficacy of Capecitabine Monotherapy in Patients with Recurrent and Metastatic Nasopharyngeal Carcinoma Pretreated with Platinum-Based Chemotherapy," Proc. Am. Soc. Clin. Oncol., vol. 22, p. 511, 2003.

Clarke, A. et al., "Predicting the Time Course of Individual Objects with MEG," Cerebral Cortex, Oxford Journals, Sep. 2014, 12 pages.

Ehrlanger et al., "Cutaneous Absorption and Urinary Excretion of 6-14C-5-5-Fluorouracil Ointment Applicated in an Ointment to Healthy and Diseased Human Skin," Dermatologies, vol. 140, Suppl. 1, pp. 129-136, 1970.

Elasmer et al., "Case Report: Hand-Foot Syndrome Induced by Oral Fluoropyrimidine S-1." Jpn. J. Clin. Oncol., vol. 3(4), p. 172-174, 2001.

Extended European Search Report, European Patent Application No. 17776577.3, dated Nov. 7, 2019, 8 pages.

Findlay, M. et al., "Measurement of Plasma 5-Fluorouracil by High-Performance Liquid Chromatography with Comparison of Results to Tissue Drug Levels Observed Using in Vivo 19F Magnetic Resonance Spectroscopy in Patients in Protracted Venous Infusion with or without Interferon-.alpha.," Annals of Oncology, vol. 7(47-53), pp. 111-117, 1996.

Fischel, J-L. et al., "Experimental Arguments for a Better Understanding of Hand-Foot Syndrome Under Capecitabine", Proceedings of the American Association for Cancer Research, 2004, p. 487 (Abstract #2119), vol. 45.

Fuji, S. et al., "Effect of Coadministration of Uracil or Cytosine on the Anti-Tumor Activity of Clinical Doses of 1-(2-Tetrahyrofuryl)-5-Fluorouracil and Level of 5-Fluorouracil in Rodents," Gann., vol. 70, pp. 209-214, 1979.

Fukushima, S. et al., "Carcinogenicity of Uracil, a Nongenotoxic Chemical, in Rats and Mice and Its Rationale", Cancer Research, 1992, pp. 1675-1680, vol. 52.

Gallen, C.C. et al., "Magnetoencephalography and Magnetic Source Imaging: Capabilities and Limitations", Functional Neuroimaging, 1995, pp. 227-249, vol. 5.

Gallo, R. et al., "The Enzymatic Mechanisms for Deoxihymidine Synthesis in Human Leukocites," The Journal of Clinical Investigation, vol. 48, pp. 82-93, 1969.

Georgopoulos, A. et al., "Synchronous Neural Interactions Assessed by Magnetoencephalography: A Functional Biomarker for Brain Disorders", Journal of Neural Engineering, 200, pp. 349-355, vol. 4.

Giani, A.S. et al., "Detecting Tones in Complex Auditory Scenes", NeuroImage, 2015, vol. 122, pp. 203-213.

Gmehlin, D. et al., "Age Effects on Preattentive and Early Attentive Auditory Processing of Redundant Stimuli: Is Sensory Gating Affected by Physiological Aging?" Journal of Gerontology A Biol. Sci. Med Sci., 2011, pp. 1043-1053, vol. 10.

Golubic, SJ et al., "MEG biomarker of Alzheimer's disease: Absence of a prefrontal generator during auditory sensory gating," Hum. Brain Mapp., 2017, vol. 38, pp. 5180-5194.

Goodman & Gilman, The Pharmacological Basis of Therapeutics, 9.sup.th Edition, pp. 1225-1229, 1996.

Gramfort, A., et al. "Graph-Based Variability Estimation in Single-Trial Event-Related Neural Responses," IEEE Trans. on Biomedical Engineering, May 2010, vol. 57, No. 5, pp. 1051-1061.

Hamalainen, M. et al., "Magnetoencephalography—Theory, Instrumentation, and Applications to Noninvasive Studies of the Working Human Brain", Reviews of Modern Physics, Apr. 1993, pp. 413-497, vol. 65, No. 2.

Hari, R., "The Neuromagnetic Method in the Study of the Human Auditory Cortex," Auditory Evoked Magnetic Fields and Electric Potentials, by Grandori et al. ed., Karger: Basel, Switzerland, 1990, pp. 222-282.

Hartmann, H.R. et al., "Modulation of the Effects of Fluoropyrimidines on Toxicity and Tumor Inhibition in Rodents by Uridine and Thymidine," Med. Oncol. & Tumor Pharmacother., vol. 3(2), pp. 111-118, 1986.

Harvey, S.C., "Drub Absorption, Action and Disposition," Chapter 35 in Remington's Pharmaceutical Sciences, 18.sup.th Ed., Gennaro et al. (eds.), 1990, Mack Publishing Co., Easton, PA, pp. 697-724.

Harvey, S.C., "Topical Drugs," Chapter 38 in Remington's Pharmaceutical Sciences, 18.sup.th Ed., Gennaro et al. (eds.), 1990, Mack Publishing Co., Easton, PA, pp. 757-773.

Hatfield, D. et al., "Synthesis of (3-Ribosyluric Acid) 5-Phosphate and (3-Ribosylxanthine) 5-Phosphate by a Pyrimidine Ribonucleotide Pyrophosphorylase of Beef Erythrocytes," The Journal of Biological Chemistry, pp. 60-66, 1964.

Hejna, M. et al., "Decrease of Duration and Symptoms in Chemotherapy-Induced Oral Mucositis by Topical GM-CSF: Results of a Prospective Randomised Trial," European Journal of Cancer, vol. 37(16), pp. 1994-2002, 2001.

Hirata, K. et al., "Pharmacokinetic Study of S-1, A Novel Oral Fluorouracil Antitumor Drug," Clinical Cancer Research, Aug. 1999, pp. 2000-2005, vol. 5.

Hoff, P., "The Tegafu-Based Dihydropyrimidine Dehydrogenase Inhibitory Fluoropyrimidines, UFT/Leucovorin (Orzel.TM.) and S-1: A Review of Their Clinical Development and Therapeutic Potential," Investigational New Drugs, 2000, pp. 153-163, vol. 18.

Ichikawa, W. et al., "Both Gene Expression for Orotate Phosphoribosyltransferase and its Ratio to Dihydropyrimidine Pehydrogenase Influence Outcome Following Fluoropyrimidine-Based Chemotherapy for Metastatic Colorectal Cancer," British Journal of Cancer, 2003, pp. 1486-1492, vol. 89.

Ikenaka, K. et al., "Effect of Uracil on Metabolism of 5-Fluorouracil In Vitro," Gann., vol. 70, pp. 353-359, 1979.

International Search Report and Written Opinion, Patent Cooperation Treaty Application No. PCT/US2013/047289, dated Feb. 11, 2014, 12 pages.

International Search Report and Written Opinion, Patent Cooperation Treaty Application No. PCT/US2017/024813, dated Aug. 14, 2017, seventeen pages.

International Search Report and Written Opinion, Patent Cooperation Treaty Application No. PCT/US2018/054228, dated Dec. 11, 2018, eighteen pages.

Jacobi, M., "Brainwaves and Consciousness—Brainwaves (1) Beta, Alpha, Theta and Delta," 2002-2014, May be Retrieved at<URL:http://www.hirnwellen-und-bewusstsein.de/brainwaves_ 1.html, Jan. 18, 2008.

Johnson, M.R. et al., "Life Threatening Toxicity in a Dihydropyrimidine Dehydrogenase-Deficient Patient After Treatment with Topical 5-Fluorouracil," Clinical Cancer Research, Aug. 1999, pp. 2006-2011, vol. 5.

Kawaguchi, Y. et al., "Studies on the Metabolism of 1-(2-Tetrahydrofuryl)-5-Fluorouracil and Uracil Co-Administered Orally to Tumor-Bearing Rats," Gann., vol. 19, pp. 869-899, 1980.

Knuutila, J. et al., "Large-Area Low-Noise Seven-Channel DC Squid Magnetometer for Brain Research," Rev. Sci. Instrum., Nov. 1987, pp. 2145-2156, vol. 58.

Kowanko et al., Prevention and Treatment of Oral Mucositis in Cancer Patients, Best Practice, 1998, pp. 1-6, vol. 2, Issue 3. Available at http:/Joralcancerfoundation_org/dental/pdf/mucositis.pdf, 6 pages.

(56) References Cited

OTHER PUBLICATIONS

Largillier, R. et al., "Prospective Analysis of Dihydropyrimidine Dehydrogenase (DPD) Activity for Predicting Capecitabine-Related Toxicities in Metastatic Breast Cancer Patients," (Roser Abstract), p. 39, 2002.

Laukka, E.J. et al., "Effects of Between-Person Differences and Within-Person Changes in Symptoms of Anxiety and Depression on Older Age Cognitive Performance," Psychological Medicine, 2017, pp. 1350-1358.

Leo, S. et al., "Dermatological Toxicity from Chemotherapy Containing 5-Fluorouracil," Journal of Chemotherapy, vol. 6(6), pp. 2-5, 1994.

Levy, S. et al., "A Pharmacokinetic Evaluation of 0.5% and a 5% Fluorouracil Topical Cream in Patients with Actinic Keratosis," Clinical Therapeutics, vol. 23(6), pp. 908-920, 2001.

Luccioni et al., "Pyrimidine Nucleotide Metabolism in Human Colon Carcinomas: Comparison of Normal Tissues Primary Tumors and Xenografts," Int. J. Cancer, vol. 58, p. 32-.

MacKean, M. et al., "Phase I and Pharmacologic Study of Intermittent Twice-Daily Oral Therapy with Capecitabine in Patients with Advanced and/or Metastatic Cancer," Journal of Clinical Oncology, vol. 16(9), pp. 2977-2985. 1998.

Maehara, Y. et al., "Scientific Basis for the Combination of the Tegafur with Uracil," Oncology, vol. 11(9), Supplement No. 10, pp. 14-21, 1997.

Makris, N. et al., "Human Cerebral Cortex: A System for the Integration of Volume- and Surface-Based Representations," NeuroImage, pp. 139-153, 2006, vol. 33.

Malet-Martino, M. et al., "Clinical Studies of Three Oral Prodrugs of 5-Fluorouracil (Capecitabine, UFT,S-1): A Review,",\The Oncologist, 2002, pp. 288-323, vol. 7.

Miller, G., "Feedback from Frontal Cortex May Be a Signature of Consciousness", Science, May 13, 2011, p. 779, vol. 332.

Mountz, J.M. et al., "Comparison of Qualitative and Quantitative Imaging Characteristics of 11C PiB and (18F)flutematamol in normal control and Alzheimer's subjects," NeuroImage Clinical, 2015, pp. 593-598, vol. 9.

Naguib, F.N.M. et al., "Enzymes of Uracil Catabolism in Normal and Neoplastic Human Tissues," Cancer Research, Nov. 1985, pp. 5405-5412, vol. 45.

Nairn, J. G., "Solutions, Emulsions, Suspensions and Extracts," Chapter 83 in Remington's Pharmaceutical Sciences, 18$^{th}$ Edition, Gennaro et al.(eds.), Mack Publishing Co., Easton, PA, 1990, only pp. 1519-1544 supplied.

Nesselroade, J.R. et al., "Methodological and Theoretical Implications of Intraindividual Variability in Perceptual-Motor Performance," Journal of Gerontology, 2004, vol. 59B, No. 2, pp. P49-P55.

Niedzwicki, J. et al., "Structure-Activity Relationship of Pyrimidine Base Analogs of Ligands of Orotate Phosphoribosyltransferase," Biochemical Pharmacology, vol. 33(15), pp. 2383-2395, 1984.

Park, D. et al., "Activation of CaMKIV by Soluble Amyloid-β1-42 Impedes Trafficking of Axonal Vesicles and Impairs Activity-Dependent Synaptogenesis," Science Signaling, Jul. 11, 2017, vol. 10, No. 487, 12 pages.

Pekkonen, E. et al., "Impaired Preconscious Auditory Processing and Cognitive Functions in Alzheimer's Disease," Clinical Neurophysiology, 1999, vol. 110, pp. 1942-1947.

Powis, G., "Anticancer Drugs: Antimetabolite Metabolism and Natural Anticancer Agents," International Encyclopedia of Pharmacology and Therapeutics, pp. 42-50, 1994.

Pugh et al. (eds.), Stedman's Medical Dictionary, 27th Edition, Lippincott Williams & Wilkins, Baltimore, MD, 2000, see pp. 365, 613-617 & 620 ("carcinoma," "dermatitis," "dermatosis & dermatoses").

Roberts, T.P.L. et al., "MEG Detection of Delayed Auditory Evoked Responses in Autism Spectrum Disorders: Towards an Imaging Biomarker for Autism", Autism Research, Feb. 2010, pp. 8-18, vol. 3, No. 1.

Sabbagh, M.N. et al., "Increasing Precision of Clinical Diagnosis of Alzheimer's Disease Using a Combined Algorithm Incorporating Clinical and Novel Biomarker Data," Neurol. Ther., 2017, vol. 6, (suppl 1), pp. S83-S95.

Samid, D., "Important Information About Xeloda (Capecitabine) Tablets," Roche Laboratories Inc., 2003, pp. 29-31.

Sawada, N. et al., "Induction of Thymidine Phosphorylase Activity and Enhancement of Capecitabine Efficacy by Taxol/Taxotere in Human Cancer Xenografts," Clinical Cancer Research, Apr. 1998, pp. 1013-1019, vol. 4.

Schilsky, R.L. et al., "Sixty-Third Meeting of the Oncologic Drug Advisory Committee," Food and Drug Administration Center for Drug Evaluation and Research, 1999.

Senff, H. et al., "Topical 5-Fluorouracil Solution in the Treatment of Warts—Clinical Experience and Percutaneous Absorption," British Journal of Dermatology, vol. 118, pp. 409-414, 1968.

Sigma U.S. Catalog, "Biochemical and Reagents for Life Science Research," St. Louis, MO, 2000-2001 edition, only p. 1000 supplied.

Sludden, J. et al., "Liver Dihydropyrimidine Dehydrogenase Activity in Human, Cynomolgus Monkey, Rhesus Monkey, Dog, Rat and Mouse," Pharmacology, pp. 276-280, 1998.

Spicer, E. et al., "Toxicity Study of Uracil in Dogs," Journal of Applied Toxicity, vol. 5, pp. 199-204, 1985.

Stein, J.H. et al., Editor-in-Chief, Internal Medicine, 4.sup.th Edition, Chapters 71 and 72, pp. 699-715, 1994.

Stokes, M. G., et al. "Simple Metric for Scaling Motor Threshold Based on Scalp-Cortex Distance: Application to Studies Using Transcranial Magnetic Stimulation," Journal of Neurophysiology, 2005, pp. 4520-4527, vol. 94, No. 6.

Supplementary Partial European Search Report for EP13810531.7, dated Feb. 10, 2016, 7 pages.

Sweatt, J.D., "Creating Stable Memories," Science, Feb. 18, 2011, pp. 869-870, vol. 331.

Swinyard, E.A. et al., "Pharmaceutical Necessities," Chapter 66 in Remington's Pharmaceutical Sciences, 18.sup.th Ed., Gennaro et al. (eds.), 1990, Mack Publishing Co., Easton, PA, pp. 1286-1329.

Taulu, S. et al., "Removal of Magnetoencephalographic Artifacts with Temporal SignalSpace Separation: Demonstration With Single-Trial Auditory-Evoked Responses," Human Brain Mapping, 2009, pp. 1524-1534, vol. 30.

Taulu, S. et al., "Spatiotemporal Signal Space Separation Method for Rejecting Nearby Interference in MEG Measurements," Physics in Medicine and Biology, 2006, 11 pages, vol. 51, No. 7.

Taulu, S. et al., "Suppression of Interference and Artifacts by the Signal Space Separation Method," Brain Topography, Summer 2004, pp. 269-275, vol. 16, No. 4.

U.S. Appl. No. 60/355,764, filed Feb. 12, 2002, Inventor John P. Ford.

U.S. Appl. No. 60/697,910, filed Jul. 8, 2005, Inventor John P. Ford.

U.S. Appl. No. 60/933,038, filed Jun. 4, 2007, Inventor John P. Ford.

U.S. Appl. No. 61/069,031, filed Mar. 12, 2008, Inventor John P. Ford.

U.S. Appl. No. 61/666,171, filed Jun. 29, 2012, Inventor John P. Ford.

U.S. Appl. No. 62/315,376, filed Mar. 30, 2016, Inventor John P. Ford.

Vanden Heuvel, J.P. et al., "Differential Nucleobase Protection Against 5-Fluorouracil Toxicity for Squamous and Columnar Cells: Implication for Tissue Function and Oncogenesis," Investigational New Drugs, Jul. 1, 2015, pp. 1003-1011, vol. 33.

Venes et al.(eds.), Taber's Cyclopedic Medical Dictionary, 21st Edition, F. A. Davis Co., Philadelphia, PA, 2009, see pp. 285-289 ("carcinoma").

Wang, J. et al., "Oral 5-FU is a More Effective Antimetastatic Agent than UFT," Anticancer Research, 2004, pp. 1353-1360, vol. 24.

Weast et al., CRC Handbook of Chemistry and Physics, Boca Raton, FL, 1981, only p. C-536 supplied: see entry for "Uracil."

Williamson, S.J. et al., "Biomagnetism," Journal of Magnetism and Magnetic Materials, 1981, pp. 129-201, vol. 22, No. 2.

Zamrini, E. et al., "Magnetoencephalography as a Putative Biomarker for Alzheimer's Disease," International Journal of Alzheimer's Disease, 2011, pp. 1-10, vol. 2011.

(56) References Cited

OTHER PUBLICATIONS

Zografi et al., "Disperse Systems," Chapter 19 in Remington's Pharmaceutical Sciences, 18.sup.th Ed., Gennaro et al. (eds.), 1990, Mack Publishing Co., Easton, PA, only pp. 257-309 supplied. See in particular p. 302 ("Emulsifying Agents").
Extended European Search Report, European Patent Application No. 18864067.6, dated Nov. 11, 2020, eight pages.
Gramfort, A., et al., "MEG and EEG data analysis with MNE-Python," Frontiers in Neuroscience, 2013, vol. 7, Article 267, pp. 1-13.
International Search Report and Written Opinion, Patent Cooperation Treaty Application No. PCT/IB2020/053219, dated Sep. 4, 2020, seventeen pages.
Extended European Search Report, European Patent Application No. 20782636.2, 9, dated Dec. 9, 2022, 14 pages.
International Search Report and Written Opinion, Patent Cooperation Treaty Application No. PCT/US2022/045839, dated Jan. 27, 2023, 23 pages.
Nichols, T., et al., "Nonparametric permutation tests for functional neuroimaging: A primer with examples", Human Brain Mapping, vol. 15, Issue 1, Jan. 2002, pp. 1-25, XP055291962, ISSN: 1065-9471, DOI: 10.1002/hbm.1058.
United States Office Action, U.S. Appl. No. 17/745,115, filed Nov. 18, 2022, 7 pages.
Demopoulos, C., et al., "Magnetoencephalographic Imaging of Auditory and Somatosensory Cortical Responses in Children with Autism and Sensory Processing Dysfunction," Frontiers in Human Neuroscience, May 2017, vol. 11, Article 259, pp. 1-15.
Baillet, S., "Magnetoencephalography for brain electrophysiology and imaging," Nature Neuroscience, vol. 20, No. 3, Mar. 2017, pp. 327-339.
Brookes, M.J. et al. "Magnetoencephalography with optically pumped magnetometers (OPM-MEG): the next generation of functional neuroimaging," Trends in Neurosciences, vol. 45, No. 8, Aug. 2022, pp. 621-634.
Grubbs, F.E., "Sample Criteria for Testing Outlying Observations," The Annals of Mathematical Statistics, vol. 21, No. 1, Mar. 1950, pp. 27-58.
Hanna-Pladdy, B. et al., "Functional Magnetic Resonance Imaging Biomarkers Predicting Cognitive Progression in Parkinson Disease: Protocol for a Prospective Longitudinal Cohort Study," JMIR Research Protocols, vol. 8, Iss. 4:e12870, Apr. 2019, pp. 1-13.
Hurd, M.D et al., "Monetary Costs of Dementia in the United States," The New England Journal of Medicine 368(14), Apr. 2013, pp. 1326-1334.
Joshi, A. et al., "Reducing between scanner differences in multi-center PET studies," NeuroImage, vol. 46, Feb. 6, 2009, pp. 154-159.
Krashes, M.J. et al., "Rapid, reversible activation of AgRP neurons drives feeding behavior in mice," The Journal of Clinical Investigation, vol. 121, No. 4, Apr. 2011, pp. 1424-1428.
Lezak, M., "Neuropsychological Assessment," Fifth Edition, Oxford, UK: Oxford University Press, Mar. 22, 2012 (table of contents only).
Logothetis, N.K. "What we can do and what we cannot do with fMRI," Nature, vol. 453(7197), Jun. 12, 2008, pp. 869-878.
López-Sanz, D. et al., "Magnetoencephalography applied to the study of Alzheimer's disease," Progress in Molecular Biology and Translational Science, vol. 165, 2019, pp. 25-61.
Mason, J.W. et al., "Recommendations for the Standardization and Interpretation of the Electrocardiogram," Circulation, vol. 115, Iss. 10, Feb. 23, 2007, pp. 1325-1332.
Medina, R. et al., "Electrophysiological Brain Changes Associated with Cognitive Improvement in a Pediatric Attention Deficit Hyperactivity Disorder Digital Artificial Intelligence-Driven Intervention: Randomized Controlled Trial," Journal of Medical Internet Research, vol. 23, No. 11:e25466, Nov. 2021, pp. 1-18.
Nunez, P. et al., "Electric Fields of the Brain: The Neurophysics of EEG," Second Edition, Oxford, UK: Oxford University Press, 2006 (table of contents only).
Poldrack, R.A., "Inferring Mental States from Neuroimaging Data: From Reverse Inference to Large-Scale Decoding," Neuron, vol. 72, No. 5 Dec. 8, 2011, pp. 692-697.
Ramirez, S. et al., "Creating a False Memory in the Hippocampus," Science, vol. 341(6144), Jul. 26, 2013, pp. 387-391.
Sherkow, J.S., "CRISPR: Pursuit of profit poisons collaboration," Nature, vol. 532(7598), Apr. 14, 2016, pp. 172-173.
Vogel, J.W. et al., "Four distinct trajectories of tau deposition identified in Alzheimer's disease," Nature Medicine, vol. 27(5), Apr. 29, 2021, pp. 871-881.
Wang, Y. et al., "Viral vectors as a novel tool for clinical and neuropsychiatric research applications," General Psychiatry 31(2), Oct. 2018, pp. 1-9.

| Discriminant, reliable, and stable features | | | |
|---|---|---|---|
| Feature | Value | Normal range | Status |
| Fraction of epochs with all 3 peaks (%) | 31 | 29 to 58 | Normal |
| Fraction of epoch with peak A (%) | 77 | 61 to 75 | ABNORMAL |
| Peak B amplitude in weaker A peaks (n.u.) | 453 | 460 to 562 | ABNORMAL |
| Amount of peak C (n.u.) | 492 | 466 to 639 | Normal |

| Signal characteristic features | | | |
|---|---|---|---|
| Feature | Value | Normal range | Status |
| Average peak A latency (ms) | 78 | 65 to 98 | Normal |
| Variability in peak A latency (ms) | 1 | -3 to 6 | Normal |
| Average peak B latency (ms) | 128 | 114 to 149 | Normal |
| Variability in peak B latency (ms) | 0 | 0 to 2 | Normal |
| Average peak A onset (ms) | 39 | 3 to 63 | Normal |
| Variability in peak A onset (ms) | 15 | 0 to 20 | Normal |
| Average peak B onset (ms) | 109 | 88 to 130 | Normal |
| Variability in peak B onset (ms) | 1 | 0 to 1 | Normal |
| Average peak B offset (ms) | 151 | 153 to 188 | ABNORMAL |
| Variability in peak B offset (ms) | 4 | 0 to 5 | Normal |
| Average peak B duration (ms) | 41 | 33 to 92 | Normal |
| Variability in peak B duration (ms) | 4 | 0 to 6 | Normal |

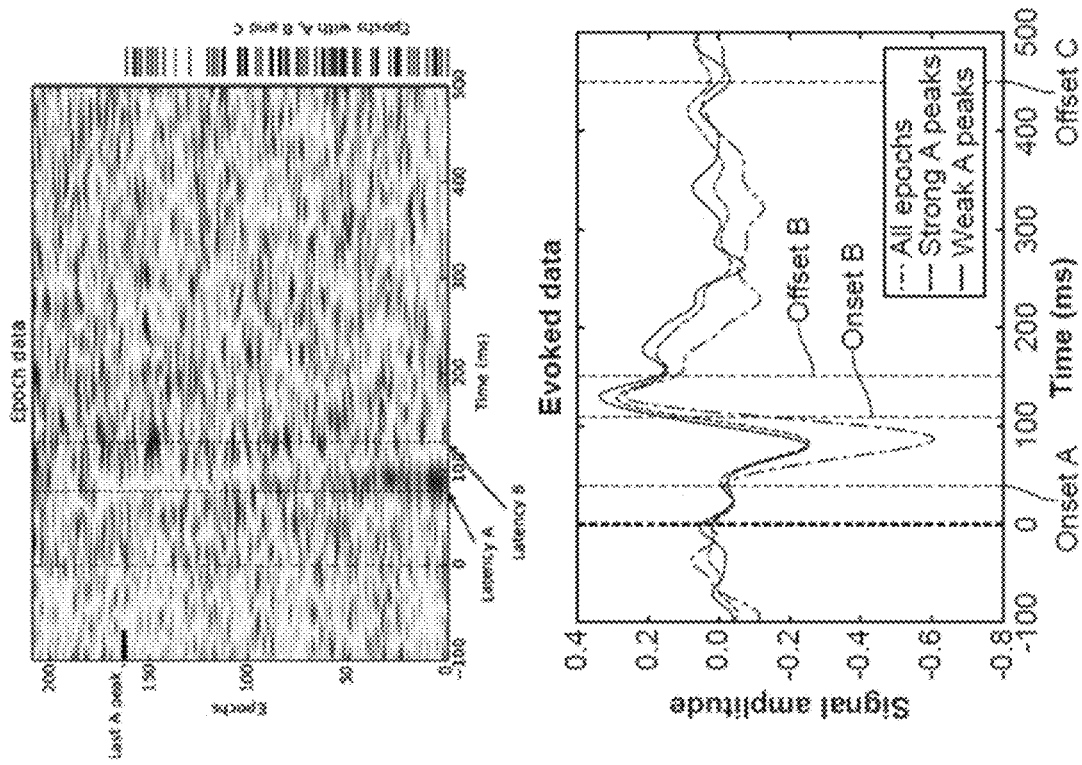

FIG. 5

METHODS AND MAGNETIC IMAGING DEVICES TO INVENTORY HUMAN BRAIN CORTICAL FUNCTION

CROSS-REFERENCE TO RELATED APPLICATIONS

This application is a continuation of U.S. patent application Ser. No. 15/472,130 filed on Mar. 28, 2017, allowed, which claims priority to U.S. Provisional Application Ser. No. 62/315,376, filed Mar. 30, 2016, all of these applications are incorporated herein by reference in their entirety for all purposes.

FIELD OF THE ART

The present description is directed to the field of medical imaging. More particularly, this description pertains to systems and methods of detecting and evaluating electrical activity in the brain.

BACKGROUND

Despite rapidly increasing societal burden, progress in developing treatments for neurodegenerative disorders, such as Alzheimer's disease ("AD"), remains slow.

Part of the challenge in developing effective therapeutic agents is the requirement that the molecule cross the blood-brain barrier ("BBB") in order to engage a disease-relevant target. Another challenge, particularly relevant to efforts to develop disease-modifying agents, is the need for noninvasive techniques that can repeatedly be used to monitor disease status and progression. Although several imaging approaches have been used to monitor efficacy of potential disease-modifying antibodies in AD clinical trials—notably positron emission tomography ("PET") detection of β-amyloid plaque burden—these radioisotopic imaging techniques detect a presumptive pathophysiological correlate of disease and do not directly measure the primary symptom, the loss of cognitive function.

Existing approaches to measuring brain function are likewise poorly suited to monitoring neurodegenerative disease status and progression.

Cerebral cortex functional imaging approaches currently in clinical use do not image neural function directly: functional magnetic resonance imaging ("fMRI") images blood flow; positron emission tomography ("PET"), when used to monitor glucose consumption, images metabolism.

In addition, there can be a mismatch between the temporal resolution of certain functional imaging approaches and the duration of signaling events in the brain. fMRI, for example, is sensitive on a time frame of seconds, but normal events in the brain occur in the time frame of milliseconds ("msec"). Although electroencephalography ("EEG") is sensitive to events in a millisecond time frame, unpredictable signal attenuation by the tissues that surround the brain cause both near and far signals to be comingled. This problem is compounded when there are multiple current sources (e.g., both primary and secondary cortical sources).

There thus exists a need in the art for noninvasive techniques for imaging brain cortical function that can be used to detect and monitor changes in function. There is a particular need for noninvasive functional imaging approaches that can be used to detect, stage, and monitor progression of neurodegenerative disorders with statistically significant classification accuracy.

SUMMARY

We have discovered that past failures to achieve adequate classification accuracies using magnetoencephalography ("MEG") to detect AD were due to the conflation of evoked responses to a repeated stimulus. Previously, it was common to average the evoked response over all such stimuli, and compare the averaged evoked responses between individuals. These initial results indicated that a single parameter based on conflated MEG data may not be sufficient to differentiate all normal test patients from all cognitively-impaired test patients based on the model MEG data. We have discovered that statistically meaningful differences between normal and diseased brain responses to a repeated stimulus are found in the relative presence and intensity of certain parameters in an individual's evoked responses across multiple distinct evoked responses; this distributional information has previously been discarded in an early step of signal analysis through averaging of those responses.

Accordingly, we have now developed models that are capable of noninvasively detecting, staging, and monitoring progression of neurodegenerative disorders with statistically significant classification accuracy.

The models separate patients having a cognitive dysfunction from patients with a normal cognitive function based on test MEG data collected from test patients' brain activity. The models are developed by collecting model MEG data from a pool of test patients having a range of cognitive function states that have been preferably objectively evaluated by an alternative protocol such as the Mini Mental State Exam ("MMSE"). The model MEG data is collected using at least one superconducting quantum interference device ("SQUID") sensor detecting signals from the brain of test patients under a data collection protocol. The MEG measures the relative extent of brain activation, excitation, and/or response. The MEG data from the at least one SQUID sensors, generally no more than one, or generally no more than a handful, is subsequently analyzed. Candidate parameters in the form of differences between the MEG scans of dysfunctional test patients and normal test patients are identified. The candidate parameters are developed to quantify these differences and to show that the activation, excitation, and/or response occurs progressively differently with progressive cognitive dysfunction. Specific ones of the candidate parameters are then selected for inclusion in one of the models as model parameters. Data science techniques of varying complexity, from regressions to machine learning and deep learning algorithms, are used to train the model for use in recognizing, quantifying, and categorizing patients outside the test set.

As a specific example, the Alzheimer's Disease Detection ("ADD") model is able to separate test patients with normal cognitive function from those with cognitive dysfunction characteristic of Alzheimer's Disease ("AD"). To train the models, MEG with a conventional set of SQUID sensors is used to detect signals from the brain following an auditory stimulus in a set of test patients. The test patients have a range of cognitive function states associated with AD that have been preferably objectively evaluated by an alternative protocol. The MEG measures, after an auditory stimulus, the relative extent of brain activation/excitation and subsequent response to the activation. Subtle differences between the MEG scans of AD test patients and "normal" test patients were identified. Discrete candidate parameters of the model MEG data were identified as model parameters and were developed to quantify these subtle differences. The models and their constituent model parameters have been shown to robustly distinguish between normal and AD patients, with performance varying from perfect categorization of the test patients downward depending on how many model parameters are used. In implementation, models may be built from among a range of possible model parameters, which concordantly have a range of performance in ability to distinguish normal and AD patients.

By examining runs on an epoch-by-epoch basis, the differences between normal and AD patients became clearer. A manifestation of cognitive competence is evident from the efficiency with which a sound stimulus elicits initially a first peak (peak A), with a higher first peak being not good, then the efficiency with which the first peak is associated with a second peak (peak B), and finally the efficiency with which the second peak is associated with a third peak (peak C). Other aspects of cognitive competence are also evident, as described with respect to a number of the other candidate parameters discussed below. Beyond the association with cognitive efficiency, perturbations in this process are stable between two sessions acquired during the same day, as well as over short time intervals (2 weeks), and are individual-specific.

In an exemplary embodiment, a method for making a determination of cognitive impairment comprises: accessing a set of epochs of magnetoencephalography (MEG) data of responses of a brain of a test patient to a plurality of auditory stimulus events; processing the set of epochs to identify a tri-peak subset of the epochs, each epoch in the subset comprising a first peak, a second peak, and a third peak; determining a plurality of parameter values by analyzing the individual epochs of the MEG data, at least one of the parameter values determined based on a count of epochs in the set having one or more of the first, second, and third peaks and at least one of the parameter values determined based on amplitudes of one of first, second, and third peaks of at least some of the epochs in the tri-peak subset; inputting the parameter values into a model that is trained based on the parameters to determine whether the test patient is cognitively impaired; and providing the determination.

In another exemplary embodiment, a method for making a determination of cognitive impairment comprises accessing a set of epochs of magnetoencephalography (MEG) data of responses of a brain of a test patient to a plurality of auditory stimulus events; processing the set of epochs to identify a tri-peak subset of the epochs, each epoch in the subset comprising a first peak, a second peak, and a third peak; determining a plurality of parameter values, at least one of the parameter values determined based on analyzing MEG data from individual epochs within at least one of the set of epochs and the tri-peak subset of epochs; inputting the parameter values into a model that is trained based on the parameters to determine whether the test patient is cognitively impaired; and providing the determination.

In yet another exemplary embodiment, a method for making a determination of cognitive impairment comprises accessing a set of epochs of magnetoencephalography (MEG) data of responses of a brain of a test patient to a plurality of auditory stimulus events; processing the set of epochs to identify a tri-peak subset of the epochs, each epoch in the subset comprising a first peak, a second peak, and a third peak; determining, a plurality of parameter values, the parameters comprising identifying a strongA subset of the epochs of the set having a strongest amplitude for the type-A peak relative to the other epochs in the set; determining a strongA_Bnum parameter representing a count of the epochs in the strongA subset having a type-B peak; identifying a weakA subset of the epochs of the set having a weakest amplitude for the type-A peak relative to the other epochs in the tri-peak subset; determining a weakA_Bamp parameter representing a measure of amplitudes of the type-B peaks of the epochs in the weakA subset; determining a weakA_Camp parameter representing a measure of amplitudes of the type-C peaks of the epochs in the weakA subset; an A*B*C parameter representing a count of the epochs in the tri-peak subset; and a nA parameter representing a count of the epochs in the set having a type-A peak; inputting the parameter values into a model that is trained based on the parameters to determine whether the test patient is cognitively impaired; and providing the determination.

Other features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 5 shows an example graphical user interface for presentation on a computer display to provide results from use of an ADD model on a test patient.

Wherever possible, the same reference numbers will be used throughout the drawings to represent the same parts.

DETAILED DESCRIPTION

I. Measurement Setup

Figure 1A:
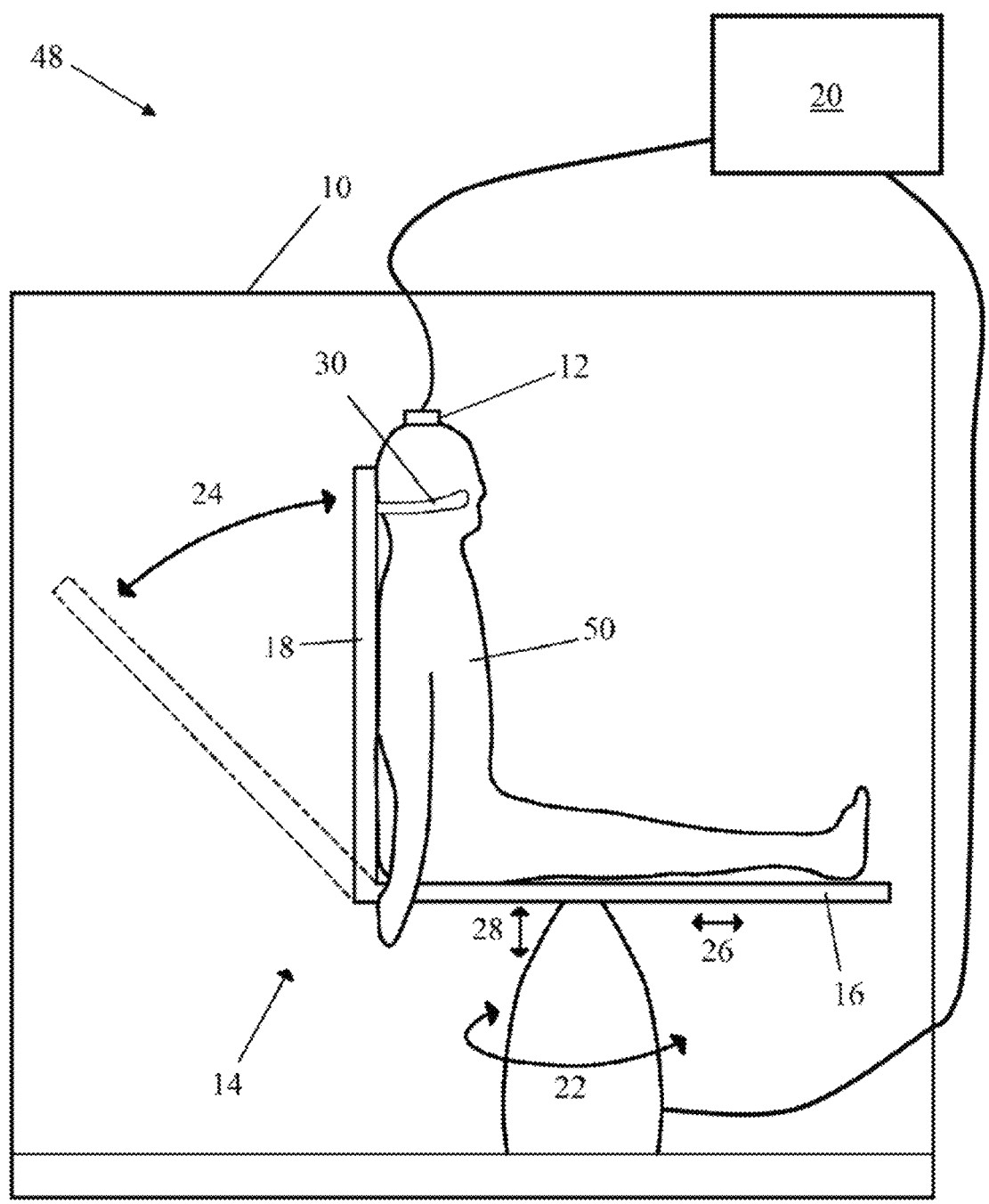
FIG. 1A shows schematically a test patient in a movable patient support device for a magnetoencephalography ("MEG") system in one embodiment.

FIG. 1A shows a Magnetoencephalography ("MEG") system 48 to detect electrical activity in the human brain, in the form of the magnetic fields generated by the electrical activity, according to one embodiment. A test patient 50 is seated in a patient support device 14. A Faraday cage 10 surrounds the test patient 50 and the patient support device 14 to block external environmental magnetic fields. The sensor head 12 and the associated Dewar housing 40 (see FIG. 1C) to cool the sensors 32 (see FIG. 1B) are fixed in space. The sensor head 12 and the patient support device 14 are in communication with and controlled by a computer 20, which is located outside the Faraday cage 10.

The patient support device 14 includes a seat portion 16 and a back portion 18. The patient support device 14 is rotatable 22 at least a full 360°, with the back portion 18 being reclinable 24, preferably from a vertical position to a position about 45° from vertical. The patient support device 14 is also controlled horizontally 26 and vertically 28 in order to maintain the sensor head 12 in contact with the head of the test patient 50, as the angle of inclination of the patient support device back 18 is simultaneously changed or the patient support device 14 is simultaneously rotated. The patient support device 14 also includes a head stabilizer 30 to maintain the head in a predetermined fixed position with respect to the patient support device back 18. The head stabilizer 30 contacts the cheeks of the test patient 50 to immobilize the cheek bones, thereby immobilizing the head.

The vertical, horizontal, rotational, and recline adjustments to the patient support device 14 may be automated and controlled by the computer 20. Alternatively, the adjustments may be manual or automated by the patient support device 14 itself. The SQUID electronics includes a monitor and a computer 20 with software for operation of the SQUID sensors 32 and control of the position of the patient support device 14. If the vertical, horizontal, rotational, and recline adjustments are done manually or independently of the computer 20, a location sensor may be used to determine the location of the head surface of the test patient 50 with respect to the SQUID sensors 32.

Figure 1B:
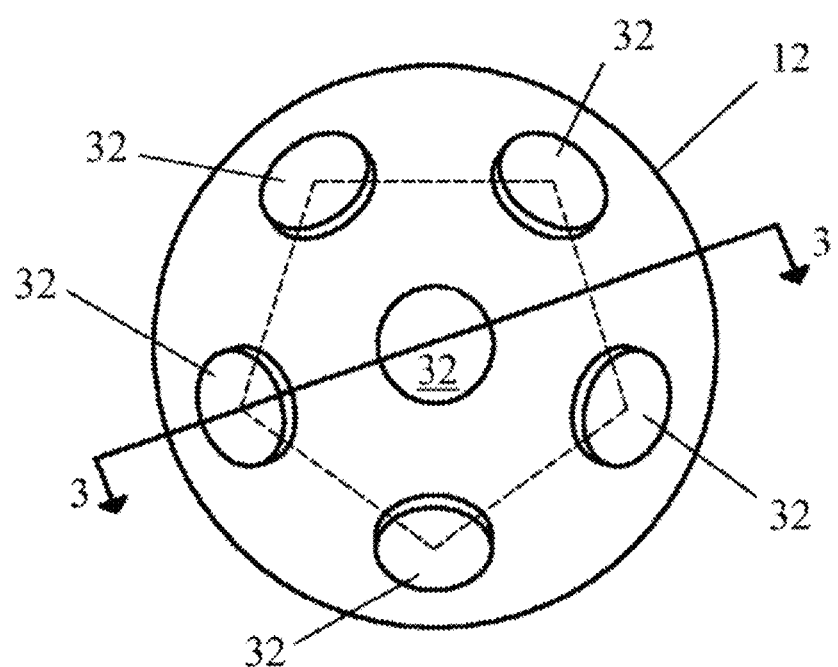
FIG. 1B shows schematically a top view of an example sensor head with an array of superconducting quantum interference device ("SQUID") sensors with the five surrounding sensors focused to an area about two to four centimeters below the central sensor in one embodiment.

FIG. 1B shows a top view of an example SQUID sensor head 12 with five SQUID sensors 32 in an array around a sixth central SQUID sensor 32, according to one embodiment. The central SQUID sensor 32 is flat with the five surrounding SQUID sensors 32 oriented at a fixed angle toward the central SQUID sensor 32. The fixed angle in FIG. 1B is about 45°. In other embodiments, other counts, orientations, and relative arrangements of SQUID sensors 32 may be used.

Although the measurement setup may comprise a currently manufactured MEG device such as an Elekta Neuromag® 306 channel (306 MEG sensor) MEG device with associated other hardware, the measurement setup may alternatively be an MEG device comprising fewer sensors and a relatively simplified measurement setup as will be further described below. This is advantageous for numerous reasons, one of which is cost. An Elekta Neuromag® 306 channel setup costs $2,000,000 at the time of this writing, whereas one embodiment of the simplified measurement setup would only cost approximately $200,000 at the time of this writing.

In some embodiments of a simplified measurement setup, the system preferably uses a single wire Faraday cage 10 for magnetic isolation. The Faraday cage 10 is a wire enclosure formed by a mesh of conducting material and blocks external static and non-static electric fields by canceling out their effects on the interior of the Faraday cage 10. The Faraday cage 10 surrounds the test patient 50 and sensor head 12.

In some embodiments of a simplified measurement setup, relatively few SQUID sensors 32, down to as few as a single sensor, are used, which reduces the equipment cost. One, two, three, four, five, six, seven, eight, or nine sensors may be used. In some embodiments, a movable patient support device 14, movable manually or by a software program, is used in conjunction with the relatively small array of SQUID sensors 32. This allows the brain region of interest (desired to be analyzed) to be precisely determined and defined (e.g., the superior temporal gyms). This helps ensure that those few SQUID sensors that are used are placed at a location around the brain identified as generating the signals desired to be analyzed. The small array SQUID sensor head 12 is lower in cost not only because of the reduced sensor count, but also because of commensurately reduced volume of liquid helium in a stationary Dewar housing 40 (see FIG. 1C) relative to the movable Dewar housing of, for example, the Elekta Neuromag® 306 system or equivalents. Further, by having SQUID sensors 32 that are not constrained to discrete, fixed locations with respect to the head of the test patient 50, the system described herein may also be able to provide significantly better images of the cortical region of interest relative to the more expensive system.

The patient support device 14 is non-magnetic and non-paramagnetic (ideally completely of plastic components) to prevent any interference with the SQUID device.

In one specific embodiment, the array of SQUID sensors 32 is fixed at a predetermined angle with respect to vertical. The predetermined angle is about 50° or less. As a specific example, the array of SQUID sensors 32 is fixed at an angle of about 45° from vertical with five SQUID sensors 32 at the points of a pentagon, each about 2 cm from a central sixth SQUID sensor 32. Each SQUID sensor 32 is about 1.5 cm in diameter. The peripheral SQUID sensors 32 are aimed at a point about 2 cm below the central SQUID sensor 32. The MEG system 48 includes a Dewar flask with a small liquid helium reservoir. The test patient 50 sits in the patient support device 14 that is tiltable up to about 45° or 50° from vertical and rotatable at least 360°, similar to a dentist chair, but with precise control of the orientation and tilt of the patient support device 14. The precise location (including both tri-axis position and orientation) of the patient support device 14 is communicated to the software of the computer 20 directing the data acquisition. The patient support device 14 stabilizes the head of the test patient 50 by a cushioned support on each maxilla. The test patient 50 and sensor head 12 are housed completely in a Faraday cage 10 to shield environmental magnetic flux. Such a device may be used anywhere, i.e., it is easily physically portable between rooms, and is expected to cost only about $200,000 at the time of this writing.

The array of SQUID sensors 32 is placed over the area of interest of the brain. The array of SQUID sensors 32 may be placed over the inferior frontal gyms to detect the "top down" response from the cortical executive region. The latter part of the 500-msec signal over the auditory cortex may likely also capture some of this information. The same strategy may be used for visual, sensory, motor, and cognitive inventory. Data collected from the array of SQUID may be used to create a regional magnetic cortical surface map to inventory the function of hearing, sight, touch, movement, and cognition of a normal healthy brain. This information may allow the analysis of individuals in disease states or other conditions of interest.

Generally, each SQUID sensor 32 in an array may function as an axial gradiometer to attenuate the environmental magnetic noise. The position of the array of SQUID sensors 32 can be correlated by an imaging of the head to give a precise location of the array of SQUID sensors 32 relative to the brain structures. Any imaging technique may be used that distinguishes the physical location and shape of the brain, including, but not limited to ultrasound and magnetic resonance imaging ("MRI"). In this case, only detected signals that demonstrate the expected strength decay laterally between SQUID sensors 32, consistent with a superficial signal origin, are scored. Software directs the movable array of SQUID sensors 32 to refine the image in order to provide a robust surface map of the surface sulcal activity, thereby specifically creating a map of basal neural activity or "noise".

In another specific embodiment, an array of three to nine or more SQUID sensors 32, about one centimeter in size with a fixed radial geometry, may be used to image the brain or the surface of the brain via a computer-directed movable C-arm.

Figure 1C:
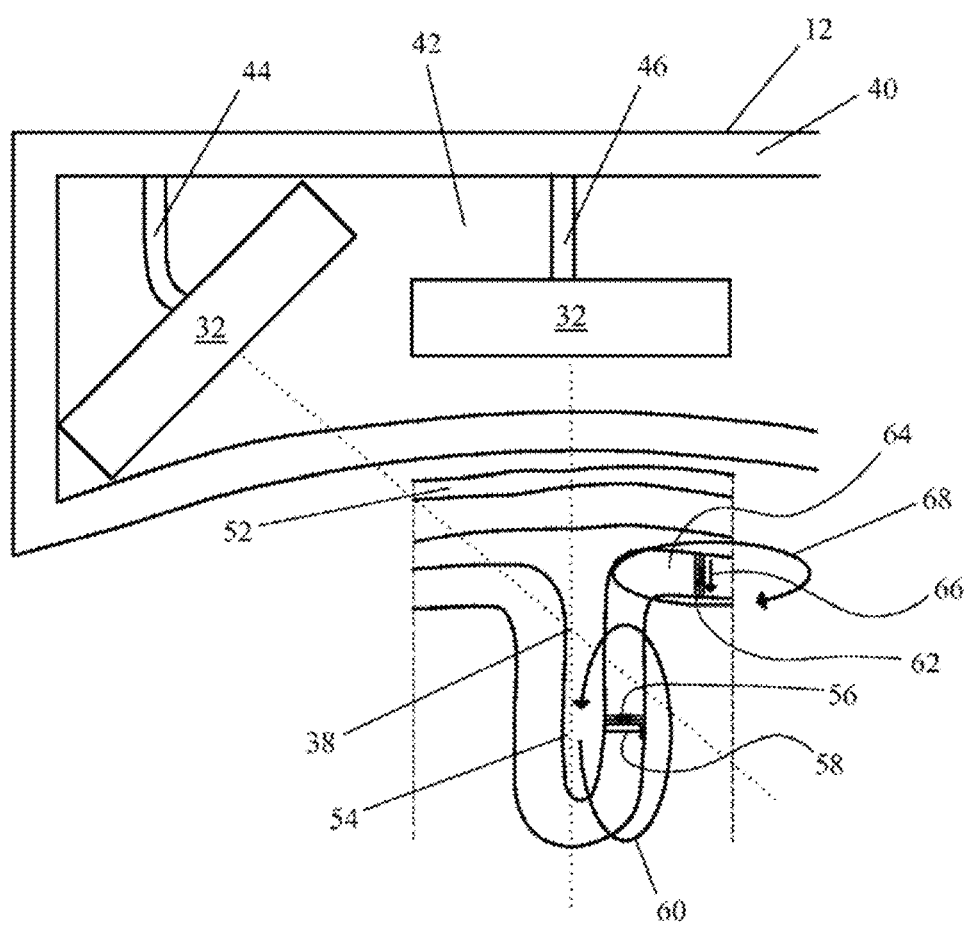
FIG. 1C shows a cross section of the SQUID sensor head of FIG. 1B along line 3-3 with the sensor head oriented to detect a magnetic field generated by electrical signals near a sulcus of a brain in one embodiment.

FIG. 1C shows the SQUID sensor head 12 placed against the scalp 52 of the test patient 50 above a sulcus 54 of interest, according to one embodiment. The peripheral SQUID sensors 32 (see also FIG. 1B) and the central SQUID sensor 32 converge on a focal point 38 about two to four centimeters below the central sensor 32. The sensor head 12 includes a Dewar housing 40 for the sensors. The Dewar housing 40 holds the liquid helium in the enclosed portion 42 of the sensor head 12 to maintain the SQUID sensors 32 at superconducting temperatures and insulates the SQUID sensors 32 and the liquid helium from the environment and the head of the test patient 50. Electrical wiring 44, 46 powers each of the SQUID sensors 32. The neuronal structures 56, and hence the electrical impulses, in the sulcal wall are oriented substantially parallel 58 to the scalp 52, thereby generating a magnetic field 60 in a plane substantially perpendicular to the scalp 52. In contrast, the neuronal structures 62, and hence the electrical impulses, of the gyms 64 are oriented substantially perpendicular 66 to the scalp 52, thereby generating a magnetic field 68 in a plane substantially parallel to the scalp 52. The magnetic field 60 generated from electrical activity in the sulcus 54 therefore is much more easily detected than the magnetic field 68 generated from electrical activity in the gyms 64 with the sensor head 12 located as shown in FIG. 1C.

The location of the source of a magnetic signal may be estimated by the SQUID sensors 32, and when the source of the magnetic signal is expected to be at a sulcus 54, the sulcus 54 location may be estimated directly from the SQUID signals. For example, when the right index finger is stimulated, the SQUID signal maximum is over the left sensory cortex, where sensory input from the finger is registered.

More generally, the sulcus 54 represents a physical boundary and an absolute limit to current transmission and thus to magnetic field transmission. That is, a SQUID sensor 32 placed contralateral to a sulcus-generated signal detects signals from, effectively, a point source, and the signal strength decreases as the inverse cube of the distance from the source. A SQUID sensor 32 placed ipsilateral to a sulcus-generated signal has characteristics of a dipole such that the signal strength decreases as the inverse square of the distance from the source. The SQUID sensors 32 contralateral to the gyms 64 of interest demonstrate a decay in intensity as the cube function of distance. In this configuration, the output is thus markedly simplified for interpretation but not degraded.

The measurement setup may also include an MRI device for collection of MRI data. This MRI data may be used to perform source localization within the brain; however, as described above, source localization may be estimated without the MRI data, such as when the magnetic signal is a well-known response from a well-known stimulus.

Figure 1D:
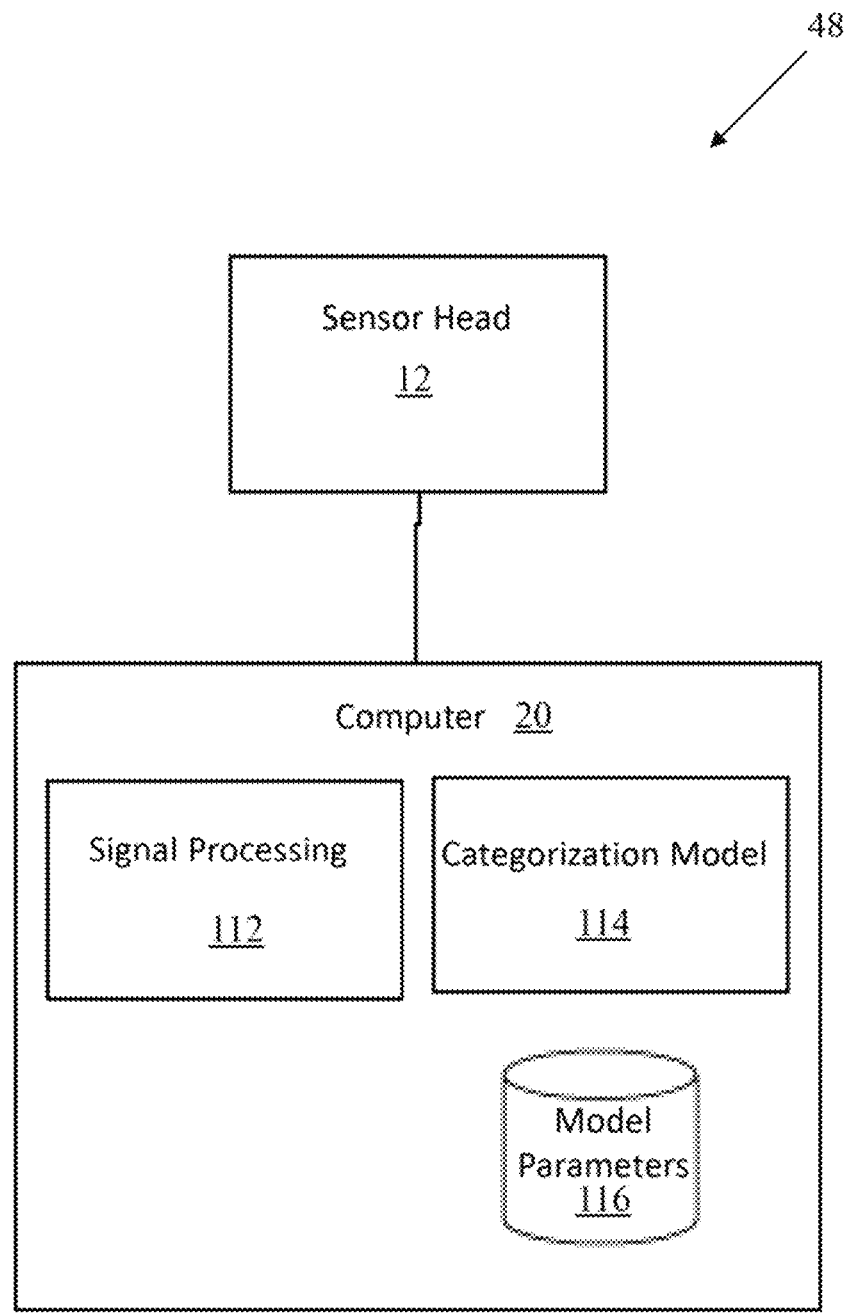
FIG. 1D shows a logical component diagram of an MEG system in one embodiment.

Referring to FIG. 1D, the MEG system 48 includes a sensor head 12 in communication with a computer 20. The computer 20 includes signal processing 112 and a categorization module 114 for determining weights of the candidate parameters of the model, and the computer 20 stores model candidate parameters 116.

II. MEG Signal Measurements

The MEG system 48 described above detects signals from the brain using one or more SQUID sensors 32 as discussed above. In one series of embodiments, these signals are captured following an auditory stimulus provided to a human patient. Generally, the models described herein are built using and can evaluate patients based on providing multiple iterations of an auditory stimulus to the patient. An "epoch", as used herein, refers to a single measured response or single output over a single predetermined period of time, such as with respect to a single stimulus event. As a specific example, to build an Alzheimer's Disease Detection ("ADD") model or evaluate any given patient with respect to the ADD model, generally multiple epochs are collected. In the experimental Example described in Section IV below the number of epochs collected was approximately 250, however this may vary by implementation.

The frequency of auditory stimulus, duration of stimulus, and pattern of stimulus may vary by implementation. For example, the patients who contributed MEG data for the generation of the example models in Section IV below were presented with a series of 700 Hz standard tones of 50 msec duration, spaced every 2500 msec. With a proportion of 1 to 5, a deviant tone (600 Hz) was randomly presented. All tones were presented to the test patient's left ear, for a total of 250 samples. Test patients were scanned in three different runs, with two of those runs being performed during the same visit. In one embodiment, only the responses to standard tones were analyzed, and responses to deviant tones were discarded.

Although specific tone frequencies, tone durations, inter-trial intervals, and numbers of epochs were used to collect the MEG data described herein, it will be appreciated that a range of values may be selected for each. The tone frequencies may be in the range of 500 to 1000 Hz or alternatively in the range of 600 to 700 Hz. The tone duration may be in the range of 25 to 75 msec. The inter-trial intervals may be at least 500 msec or alternatively in the range of 500 to 3000 msec. The total number of epoch collected in a single session may be at least 200 or alternatively at least 250.

The measurement setup and computer 20 particularly may map the magnetic field strength to the surface of the cerebral cortex. The array of SQUID sensors 32 are located over the cortical region controlling the function to be inventoried. For auditory evoked potential, the sensor heads 12 are placed over the superior temporal gyms to record initial response to a repeated sound stimulus. The patient support device 14 may be moved to refine the topological image quality. The contour maps of magnetic field intensity may be collected over a 500-600 msec epoch after a defined stimulus (e.g., pitch, intensity, duration, and repetition). To achieve adequate data homogenization in order to render the content of the collected MEG data understandable without degrading it, the data collection may be limited to neural transmission originating in the most superficial neurons lining the sulci of the relevant gyms of the human cortex. These processes were carried out with respect MEG data that served as the basis for the generation of the example models of Section IV below. The output may be presented as a contour map with no attempt being made to determine the underlying dipole or current structure.

Data collected from the MEG system that is passed to the computer 20 may be band-pass filtered, for example by retaining frequencies in the range of 1-30 Hz and removing frequencies outside that range. This helps keep most of the variance in the power of the recordings and also to remove any slow drifts in the data, normally related to recording artifacts. The data may also be otherwise processed, one example of which is segmenting an incoming data stream into separate epochs by time. For example, the computer 20 may determine the timing of the presentation of each standard tone, and data in the 100 msec preceding the presentation, and 500 msec after, may be recorded and averaged over all presentations. This procedure results in one time series per channel, containing 600 samples from −100 msec to 500 msec, where time zero determined the presentation of the standard tone. These processes were carried out with respect to MEG data that served as the basis for the generation of the example models of Section IV below. In one example scenario used to build the test ADD model described in Section IV below, the number of averaged presentations was between 207 and 224, depending on patients and runs.

Other types of signal processing may also be performed. For example, data collected by the Elekta Neuromag® 306 channel system may be further processed using Elekta Neuromag's Maxfilter™ software to remove sources of outside noise. This signal processing was carried out with respect MEG data that served as the basis for the generation of the example models of Section IV below. Depending upon the physical setting of data collection and specific data collection tools used, additional or even fewer signal processing steps than described herein may be helpful as well, particularly due to variation based on the physical location of the recording (e.g. the amount of external noise in the site). Thus, signal processing may not be necessary based on the recording instrument and site used in future applications of this description.

Figure 2A:
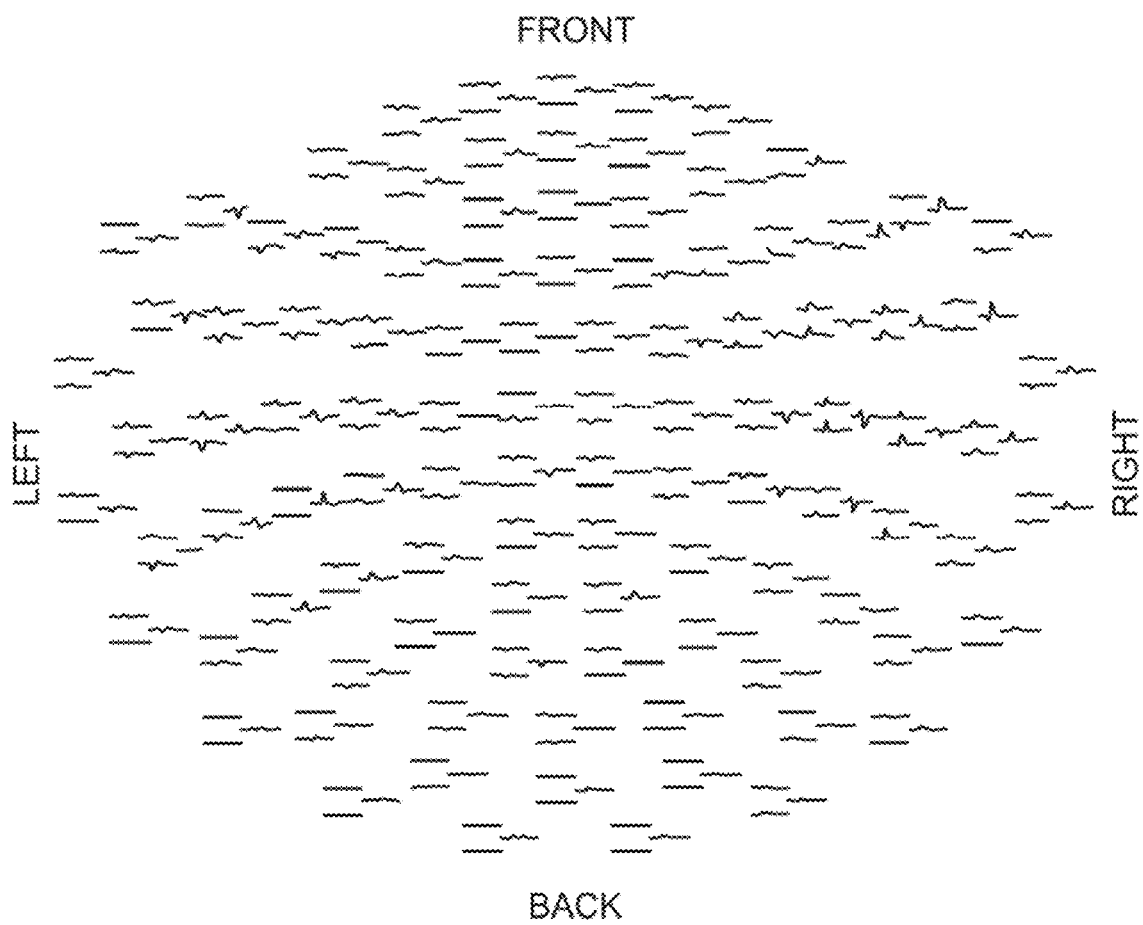
FIG. 2A shows example averaged responses to a stimulus for each of a number of SQUID sensors.

FIG. 2A illustrates the averaged response of a signal (a "signal illustration") to the standard tone for each SQUID sensor 32, both gradiometers and magnetometers, with each signal illustration being arranged in a location in FIG. 2A corresponding to the relative location of the SQUID sensor 32 in the array in the sensor head 12, according to one embodiment. Each signal illustration in FIG. 2A represents one of the 306 sensors (not separately labeled), where the horizontal axis goes from −100 to 500 msec, where 0 represents the time at which the tone was presented to the participant. As discussed above, the Y axis value for signal received from the SQUID sensor 32 is a quantification of magnetic activity measured in a particular part of the brain, as indicated by magnetic fields detected by the SQUID sensors 32.

Figure 2B:
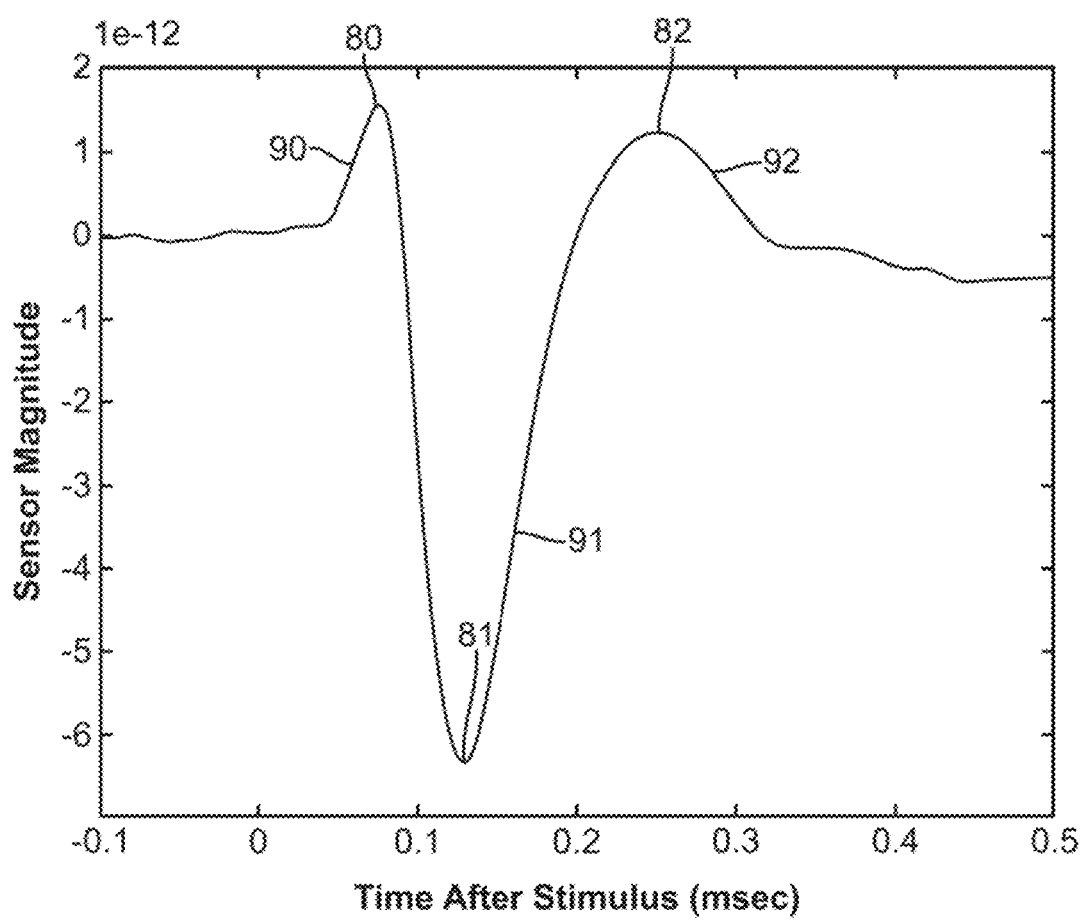
FIG. 2B shows an example averaged response for a single SQUID sensor.

Zooming in on an example SQUID sensor's response provides a prototypical waveform pattern such as shown in FIG. 2B, which shows an example of an averaged evoked stimulus response in an area of interest in the brain as measured by a single SQUID sensor 32 of the sensor head 12. The positive and negative sensor magnitude depends on the position of the sensor and are therefore arbitrary, but peak B 92 is shown and described as a negative peak throughout the present disclosure for consistency. The example waveform pattern of FIG. 2B was collected from a test patient with no measured cognitive dysfunction.

The human brain's response to the auditory stimulus, on average and for particularly placed SQUID sensors 32, includes several curves that peak, that is they have values of zero for their first derivative at some point after stimulus. These peaks include a peak A 90 defining a first local maximum 80, followed by a peak B 91 defining a local minimum 81, followed by a peak C 92 defining a second local maximum 82, followed by a return to a baseline. Peak A 90 is commonly known in the EEG literature as "P50" or "m50". Peak B 91 is commonly known in the EEG literature as "N100", "m100", or an awareness related negativity ("ARN") peak. Peak C 92 is commonly known in the electromagnetic literature as "P200". On average, the first local maximum 80 is generally observed within about 50 to 100 msec after the stimulus, which was presented at time zero in FIG. 2B. The local minimum 81 is generally observed between about 100 and 150 msec after the stimulation. The second local maximum 82 is generally observed between about 200 and 400 msec after the stimulation event.

Throughout the remainder of this description and in the claims, it is sometimes useful to refer to these peaks without reference to which specific peak is intended. For this purpose, the terms "first peak", "second peak", and "third peak" are used. Where the "first peak" is either peak A 90, peak B 91, or peak C 92, the "second peak" is a different one of the peaks from the "first peak", and the "third peak" is the remaining peak different from the "first peak" and the "second peak". For example, the "first peak" may be arbitrarily associated with peak B 91 for this example, with the "second peak" being peak A 90 and the "third peak" being peak C 92, and so on.

III. Model Development

Once MEG signals have been collected from a set of test patients 50 as model MEG data, possible candidate parameters of the model MEG data may be identified, analyzed, and selected to determine the model parameters that will make up the ADD model. The heat maps introduced in Section III.B. provide one way in which the MEG data may be analyzed for use in performing these tasks.

III.A. Sensor Selection

In developing the ADD model, consideration is given to specific signals in the sensor head 12 that are used to train and use the model. For example, for models in Section IV (except for Section IV.E) below, a pool of channels of SQUID sensors 32 located ipsilaterally to the tone presentation, where the most discriminating parameters between the two groups were initially identified, were reviewed. Within that channel pool, in one implementation the channel with the least variability in the latency of peak A 90 was chosen. Specifically, the latency of peak A 90 (e.g., the time point from stimulus presentation to maximal deflection within the expected peak A 90 timeframe) was calculated for the data from each of a group of channels previously identified to capture the ipsilateral response. That process was repeated two thousand times, sampling the epochs with replacement (bootstrap) in each iteration. This procedure yielded a distribution of latencies of peak A 90 for each channel in the pool, and the channel with smallest variability in the latency of peak A 90 was selected.

In other implementations, other or additional factors may be used to identify one or more channels whose test data will be analyzed to build the ADD model. Examples of these factors and example models built using these factors are discussed in Section IV.E below.

In other models, other criteria may be used to select one or more SQUID sensors 32 whose test data will be analyzed to build the ADD model, such as, for example, the best match to the expected 3-peak pattern (peak A 90, peak B 91, and peak C 92) or the strongest peak B 91 when responding to auditory tones.

III.B. Candidate Parameter Identification

There is a great deal of information that can be obtained from the recorded epochs of MEG signal data. On an individual epoch level or after averaging many epochs, the following pieces of information may be determined for use as candidate parameters themselves, or as precursor information towards the determination of other candidate parameters. The computer 20 may determine maximum 80 (or maximum "strength") of peak A 90, the maximum 81 of peak B 91, and the maximum 82 of peak C 92, in either absolute units of magnetic field strength, electrical activity, in some other units, or on a relative scale such as % of largest recorded epoch for that patient or relative to some baseline. The computer 20 may also determine an associated time of occurrence of each peak after stimulation, which are referred to hereafter as latency A, latency B, and latency C, respectively. Latencies may also be computed in other forms, for example the latency of peak B 91 may be calculated relative to the average peak A 90 latency, for that patient or for a population, and so on. The computer 20 may also determine an area under the curve with respect to a baseline, relative to that patient or relative to a population, for peak A 90, peak B 91, and peak C 92. The onset and offset of each peak 90, 91, 92, calculated, for example, as mean (baseline) +/−2 standard deviations, may also be useful in candidate parameter identification.

Due to the variation across epochs, valuable additional information may be obtained by analyzing the MEG data in heat maps. Visualizing this MEG data in the form of a heat map, such as the one shown in FIG. 3A, allows visual inspection of the set of raw epoch data to identify trends and parameters that are hidden or lost in averaged or otherwise collapsed or conflated MEG data. In such a heat map, each of the responses, or epochs, is plotted as a horizontal line with a color scale representing the strength of the measured magnetic field. These heat maps allow visual interpretation of the set of raw epoch data that the computer 20 processes in generating and using the ADD model. Although for convenience some of the following descriptions of the generation and use of the ADD model are described with respect to calculations that may be performed with respect to and on the data in these heat maps, those of skill in the art will appreciate that in practice the computer 20 performs calculations with respect to the data itself, without regard to how it would be visualized in a heat map.

Many candidate parameters were identified by observation of an apparent correlation between the candidate parameter and the Mini-Mental State Examination ("MMSE") score of the test patient. The apparent correlations were mostly initially identified by visual inspection of the heat maps of model MEG data. For example, it was observed that the AD test patients (i.e., test patients with lower MMSE scores) tended to have more epochs with peak A 90 than normal test patients 50. It was also observed that normal test patients (i.e., with higher MMSE scores) tended to have more epochs with all three peaks. The weaker peak A 90 half of the epochs that have peak A 90 were observed to have a higher amplitude of peak B 91 in normal test patients than AD test patients. Finally, the number of epochs with peak C 92 in the weaker peak A 90 half of the epochs that have peak A 90 were observed to be within an intermediate range for normal test patients.

Figure 3A:
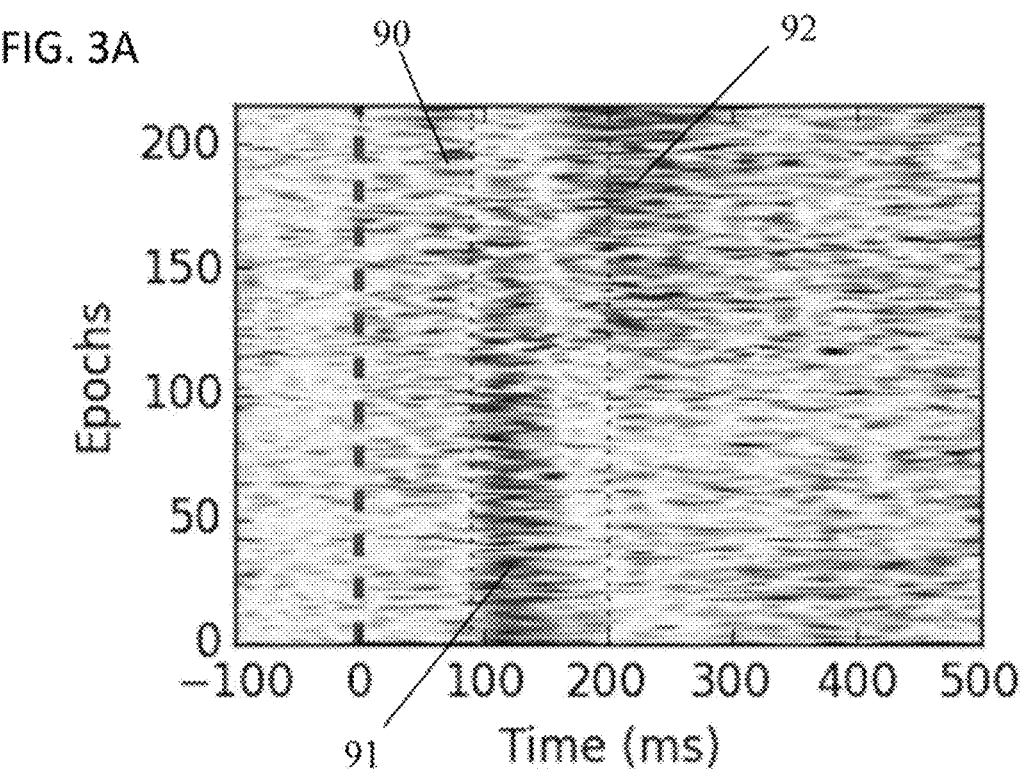
FIG. 3A shows an example heat map of the epochs of a magnetoencephalography ("MEG") set of scans from a single session for a single SQUID sensor for a first normal patient.
Figure 3B:
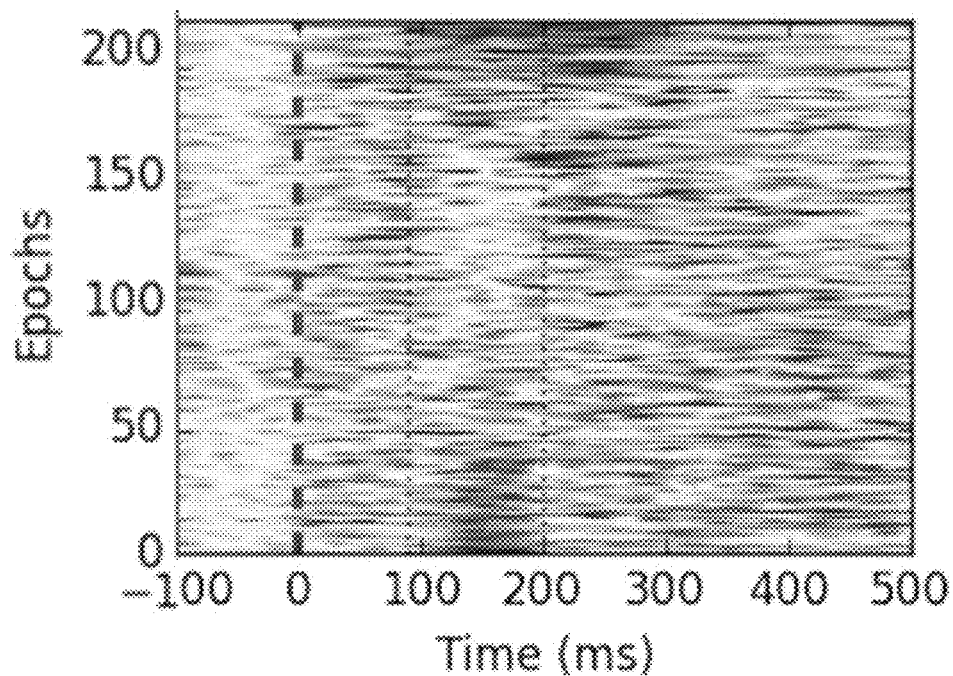
FIG. 3B shows an example heat map of the epochs of a MEG set of scans from a single session for a single SQUID sensor for an Alzheimer's Disease ("AD") patient.
Figure 3C:
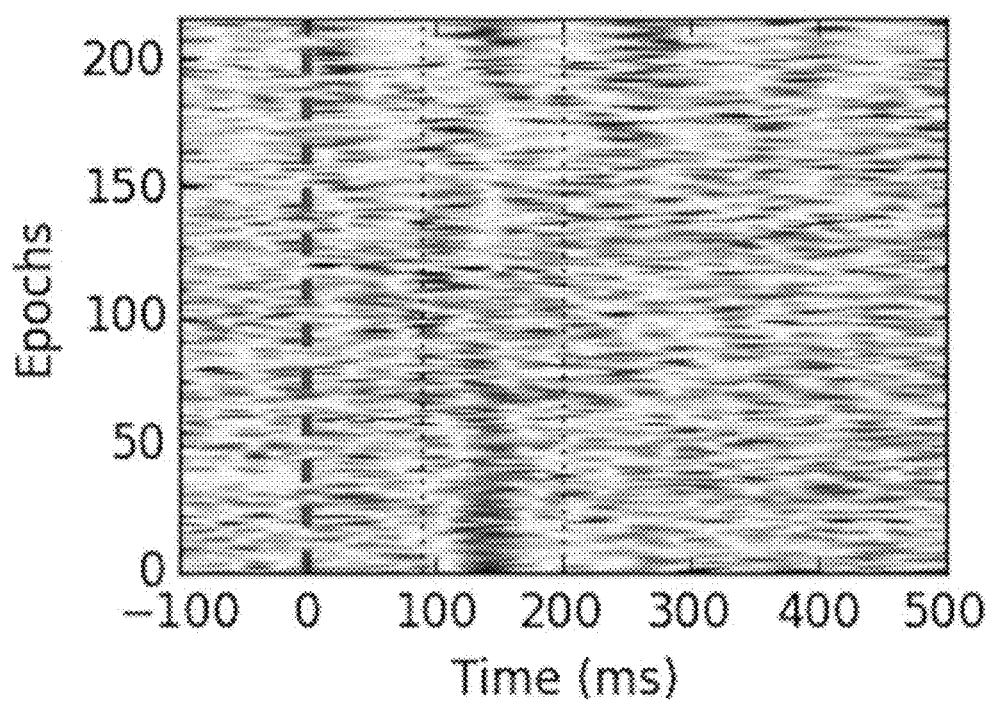
FIG. 3C shows an example heat map of the epochs of a MEG set of scans from a single session for a second normal patient.

FIG. 3A through FIG. 3C illustrate several example heat maps, with epochs on the y-axis and time with respect to the stimulus time on the x-axis. Each heat map represents one complete auditory stimulation test run for one patient. Each epoch represents a response to a single stimulus. In these heat maps, white refers to a neutral (close to baseline) magnetic or electrical field as measured by one of the SQUID sensors 32, while red arbitrarily refers to a positive magnetic or electrical field and blue arbitrarily refers to a negative magnetic or electrical field. For each epoch, the color scale is normalized from blue to red based on the data in the epoch. The relative intensity of the positive or negative field is indicated by the intensity of the red or blue color, respectively. The epochs in the heat maps of FIG. 3A, FIG. 3B, and FIG. 3C are not ordered chronologically but rather by a similarity metric of the signal within the window of peak B 91. Any one of a number of different sorting metrics may be used. For example, the epochs in the heat map may be sorted based on the duration of one of the three peaks 90, 91, 92, the maximum of one of the three peaks 90, 91, 92, or the latency of one of the three peaks 90, 91, 92. After the sorting of all epochs is done, for visual representation the highest peak B 91 is placed at the bottom in FIG. 3A through FIG. 3C.

FIG. 3A shows a heat map of the MEG data from a normal patient. Peak B 91, represented in blue between about 90 and 200 msec, has a uniform, well-defined onset and leads to a strong peak C 92, represented in red and appearing after peak B 91. In contrast, FIG. 3B shows the MEG data for an AD patient having a peak B 91 with a less-uniform, less-defined onset. In this case, the peak B 91 is not particularly strong, and although the peak C 92 is not very uniform or well-defined, it is still clearly present. Not all AD patient MEG data, however, showed this same type of deviation.

The MEG data (not shown) from one AD patient shows a stronger peak B 91 with a less-uniform, less-defined onset and a peak C 92 that is barely noticeable. MEG data (not shown) for two other AD patients shows a much stronger peak A 90 than for the MEG data of the normal patient shown in FIG. 3A. The onset of the peak B 91 was fairly uniform and well-defined for those AD patients but was delayed in comparison to peak B 91 of the normal patient, and peak C 92 was visible but weak. Finally, FIG. 3C shows MEG data for another normal patient, but the data is very atypical in comparison to the observed MEG data of the other normal patients. Peak A 90, peak B 91, and peak C 92 are fairly weak and poorly-defined in the MEG data in FIG. 3C, with peak B 91 starting later and ending earlier than for other normal patients. Collectively, these heat maps illustrate that reliance on averaged or otherwise aggregated epoch data alone obscures the variety in stimulus responses that will occur in actual patients, and thus is likely to alone be insufficient to generate a model for discriminating between normal and AD patients.

At least some of the candidate parameters for the ADD model were identified or are more easily explained by looking at the non-averaged epochs of MEG data organized in heat maps. Some of these candidate parameters include a percentage of epochs having a particular peak or combination of peaks. The determination of whether or not a given epoch has a given peak can be based on any one of a number of calculations, examples of which are described further in the following subsections of Section IV.

Additional candidate parameters include identified subsets of epochs in a given set of scans from a single session for a given SQUID sensor. Specifically, two (or more) subsets may be identified for a given test patient dividing the epochs based on any one of the candidate parameters or some other aspects. For example, two subsets may be identified, based on a candidate parameter such as presence of one of the peaks where presence is a relative measure of magnetic field strength relative to the other epochs for that test patient. In this example, the subset with the peak being present may be divided into two further subsets of a "stronger" subset including some threshold proportion of the epochs (e.g., 50%) with the higher (or stronger, or strongest) relative presence of the peak, and also of a "weaker" subset including the remaining proportion of the epochs with the lower (or weaker, or weakest) relative presence of peak (or absence thereof). Other candidate parameters or aspects of the epoch data may also be used to generate subsets, such as strong and weak subsets, including, for example, peak timing and variability, and peak amplitude and variability.

Yet additional candidate parameters may be determined based on those identified subsets. For example, any given candidate parameter mentioned in Section IV may be determined with respect to an identified subset of epochs. For example, if a strong peak A 90 subset is identified, which may represent 50% of the epochs in the set of scans from a single session of a patient having the strongest relative presence of peak A 90 compared to a weak peak A 90 subset, another candidate parameter may be the mean or median amplitude (in terms of magnetic field strength) of the peak B 91 in the strong subset. One of skill in the art will appreciate the wide variety of possible candidate parameters that may possibly be generated by dividing the epoch data from the set of scans from a single session of a patient and sensor according to one aspect/candidate parameter, and then calculating another candidate parameter based on an identified subset.

III.B.1. Candidate Timing Parameters

Some of the candidate parameters may be generally categorized as peak timing parameters, including peak latency parameters, peak onset parameters, peak offset parameters, and peak duration parameters. Each of these candidate parameters may be calculated for each of peak A 90, peak B 91, and peak C 92. For these candidate parameters, the values of the candidate parameters for the ADD model are determined based on epochs from test patient training data that are determined to include all three peaks 90, 91, 92, herein referred to as the tri-peak subset. Thus, instead of using all epochs from the scan session of a test patient 50 of a SQUID sensor 32 to calculate the value of the timing parameter for each peak, it was first determined which epochs had each peak, and then the value for the timing parameter for each peak was calculated. The average and variability of the value of each timing parameter was calculated through bootstrapping, and these averages and variabilities are additional possible ADD model candidate parameters. Additional parameters may also include the values of the timing parameters (and their averages and variabilities) as instead calculated from averaged response MEG data (i.e., the average of all epochs together per SQUID sensor per patient).

More specifically, the latency of peak B 91 may be estimated as a time point in each epoch at which the signal displayed its maximum absolute value. The values of the peak B 91 latency average ["latencyB (mean)"] and variability ["latencyB (var)"] candidate parameters for a particular model patient may be calculated based on the data set of the individual peak B 91 latency points for the epochs under consideration (e.g., those having all three peaks) for that particular model patient in the training set. The resulting candidate parameter values may then be fed into the ADD model for training.

The latency of peak A 90 may be estimated based on the time point in each epoch at which the first time derivative of the signal became zero, counting backwards from the latency of peak B 91. The values of the peak A 90 latency average ["latencyA (mean)"] and variability ["latencyA (var)"] candidate parameters may be determined based on the time points for these epochs under consideration for each patient in the training set.

Again, starting at the latency of peak B 91 and going backwards, the onset of peak B 91 may be estimated based on the time point in each epoch at which the absolute value of the signal became more than twice the standard deviation of the baseline signal (for time<0). The values of the peak B 91 onset average ["onsetB (mean)"] and variability ["onsetB (var)"] candidate parameters may be determined based on the time points for these epochs under consideration for each patient in the training set.

Similar to the onset of peak B 91, the time point in each epoch for the offset of peak B 91 may be estimated using the same criteria but counting forward from the latency of peak B 91. The values of the peak B 91 offset average ["offsetB (mean)"] and variability ["offsetB (var)"] candidate parameters may be determined based on these time points for the epochs under consideration for each patient in the training set.

Starting at the latency of peak A 90 and going backwards in time, the onset of peak A 90 may be estimated as the time point in each epoch at which the first time derivative of the signal changes sign. The values of the peak A 90 onset average ["onsetA (mean)"] and variability ["onsetA (var)"] candidate parameters may be determined based on these time points for the epochs under consideration for each patient in the training set. Note that the onset of peak B 91, as defined herein, may be the same as the offset of peak A 90. Similarly, the offset of peak B 91, as defined herein, may be the same as the onset of peak C 92.

The offset of peak C 92 was calculated as the first time point in each epoch when the signal returns to the same value as in the offset of peak B 91, or some threshold time (e.g., 450 msec post stimulation), whichever occurs sooner. The value of the peak C 92 offset average ["offsetC (mean)"] and variability ["offsetC (var)"] candidate parameters may be determined based on these time points for the epochs under consideration for each patient in the training set.

The duration of peak B 91 in each epoch is the offset of peak B 91 minus the onset of peak B 91. The values of the peak B 91 duration average ["duration (mean)"] and variability ["duration (var)"] candidate parameters may be determined based on these time points for the epochs under consideration for each patient in the training set.

For each of these timing parameters, a particular process for calculating the value of the candidate parameter is provided above, however those of skill in the art will appreciate alternative mechanisms of calculating these quantities may be established.

III.B.2. Candidate Subset Parameters

The determinations of the values of other candidate parameters for the test patients in the training set involves further processing of the epochs of the MEG data. As above, illustration by heat map is useful in conceptualizing these candidate parameters. One type of processing includes determining which epochs include one or more of the peaks. This calculation can be used for determining a number of candidate parameters, including those based on strong/weak subsets of epoch as introduced in Subsection IV.B above.

In one embodiment, to perform this processing and/or identify candidate parameters, the epochs in the heat map are sorted based on similarity within specific time windows. Often, though not necessarily, the sorting is with respect to a particular "sorting" peak. For example, the epochs in FIG. 3A may be sorted based on the time window of sorting peak B 91, such that epochs at the bottom of the plot look more similar, and are more likely to have a peak B 91, than epochs at the top. To do the sorting, initial peak boundaries are first estimated using all epochs for a test patient, and those initial estimates are used to sort the heat map and count the epochs that displayed each peak. In one embodiment, sorting is performed using spectral embedding that transforms the data to a single dimension, after applying a radial basis function ("RBF") kernel with a gamma value such as gamma=0.1.

After the epochs are sorted based on their similarity within a time window related to peak A 90, peak B 91, or peak C 92, a cutoff epoch for delineating between which epochs are determined to have and to not have the sorting peak is selected that maximizes the correlation of the sorted area within the time window. In one embodiment, an ideal linear signal decay function is used to determine the maximum of the correlation within the time window. For example, assume peak A 90 is the sorting peak and there are a total of 200 epochs. When visually examining the heat map sorted in the initial guess for peak A 90, only about the bottom 30% of the epochs had peak A 90 in one case. Computationally, to determine the cutoff epoch, the computer 20 may create 200 different images where the signal in the time window for peak A 90 linearly decays from the "bottom" of the heat map to one of the 200 epochs, and remains zero after it ends its decay. The image that has the highest correlation with the actual heat map is considered the image where the zero is around the 30% mark.

Figure 3D:
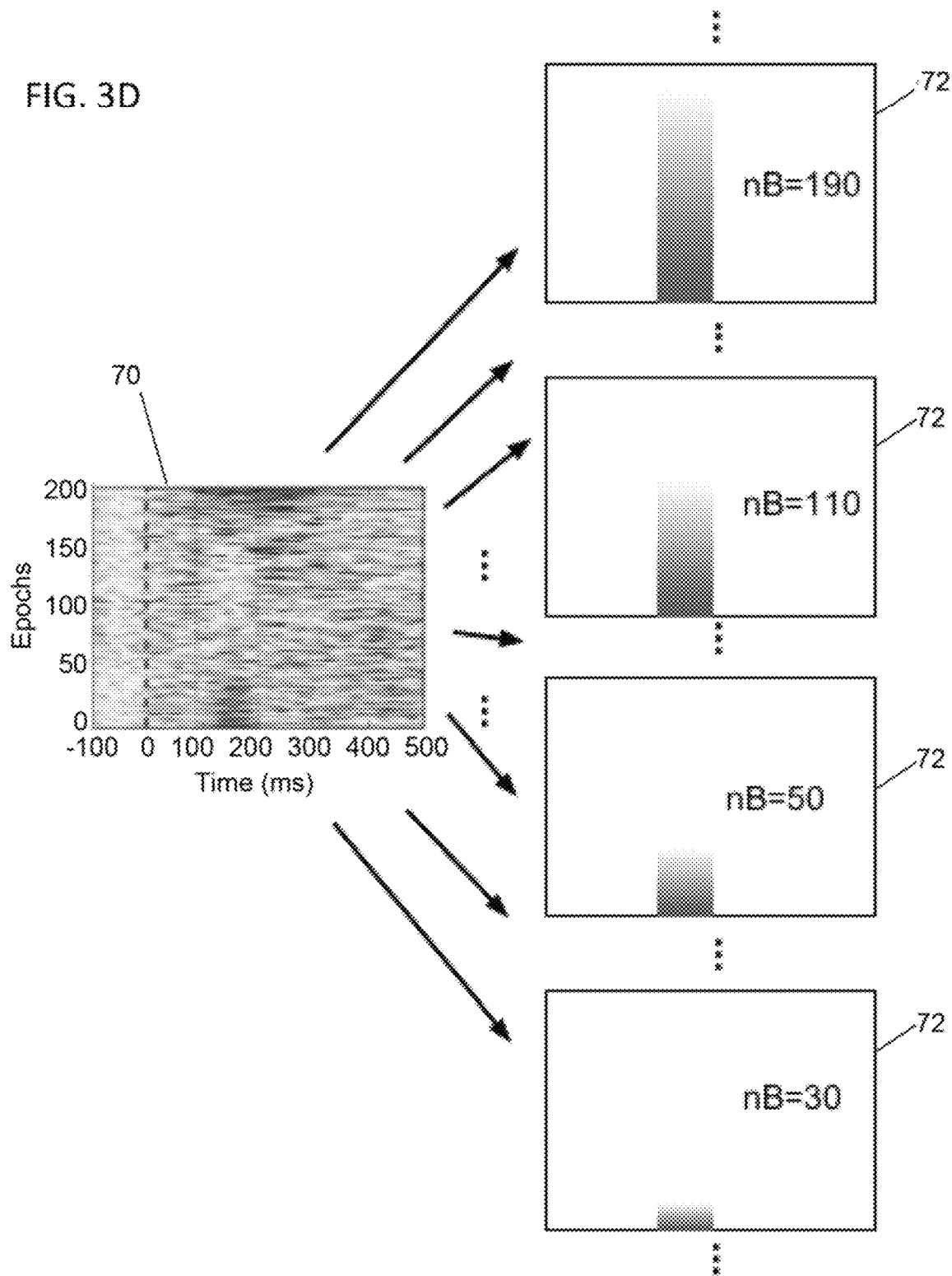
FIG. 3D shows a procedure for estimating the candidate parameter nB.

FIG. 3D schematically shows the determination of the nB value for a sample set of scans from a single session. The real heat map 70 is spatially correlated with every possible ideal heat map 72 from no epochs having peak B 91 up to all of the epochs having peak B 91. Each epoch is assigned a normalized maximum value based on the maximum value of the strongest peak B 91. For a given sample set, the peak latencies, onsets, and offsets are determined using bootstrapping. Those three timing variables are then used in determining nB (or nA or nC). The sorting of the heat map is done using only the data within the onset-to-offset time window of the peak being analyzed. After nB (or nA or nC) is determined, all of the epochs from 1 to nB (or nA or nC) are classified as having peak B 91 (or peak A 90 or peak C 92).

The ideal heat maps 72 for nB=30, nB=50, nB=110, and nB=190 are shown in FIG. 3D for the real heat map 70 having about 200 epochs. Each ideal heat map 72 has a linear gradient within the peak B 91 window, where epoch one has a value of one (e.g., dark blue) and epoch nB has a value of zero (e.g., white). The nB value for the ideal heat map 72 with the highest correlation to the real heat map 70 is assigned as the nB value for the real heat map 70. A similar approach is used to assign the values for nA and nC.

Using this approach, it can be determined which specific epochs have (or lack) each of the three peaks 90, 91, 92, and the number of epochs with each peak can be calculated, as well as how many epochs have every possible combination of the three peaks 90, 91, 92. Said differently, the tri-peak subset of epochs can be determined. Additionally, the values for a number of the candidate parameters for each patient in the training set can be determined, including the candidate parameter regarding the number of epochs with peak A 90 [nA], the candidate parameter regarding the number of epochs with peak B 91 [nB], the candidate parameter regarding the number of epochs with peak C 92 [nC], the candidate parameter regarding the number of epochs with peak A 90 and peak B 91 [A*B], the candidate parameter regarding the number of epochs with peak A 90 and peak C 92 [A*C], the candidate parameter regarding the number of epochs with peak B 91 and peak C 92 [B*C], and the candidate parameter regarding the number of epochs with peak A 90, peak B 91, and peak C 92 [A*B*C]. The values for these candidate parameters may be determined as a number count, or as a fraction of the total number of epochs for that test patient.

The values of other candidate parameters may also be determined for each test patient 50 in the training set. The values of the area of peak A 90 [areaA], area of peak B 91 [areaB], and the area of peak C 92 [areaC] candidate parameters are simply the aggregated magnitude, that is the amount of area that is blue (i.e., with positive magnetic field signal) for peak A 90 and peak C 92, respectively, and red (i.e., with negative magnetic field signal) for peak B 91 in the epochs that have been detected to contain peak A 90, peak B 91, and peak C 92, respectively. The value of an area ratio candidate parameter (e.g., [areaA/areaC], [areaA/areaB], [areaB/areaC] or any inverse thereof) is simply the ratio of these two numbers.

The values of other candidate parameters may be determined by creating strong and weak subsets, as introduced above. The value of the candidate parameter for the strong peak A 90 epochs containing peak B 91 is based on the number of epochs having a peak B 91 in the strong peak A 90 subset (e.g., half/50% cutoff) of epochs ["strongA_B- num"]. Similarly the value of the candidate parameter for the weak peak A 90 epochs containing peak B 91 is based on the number of epochs having a peak B 91 in the weak peak A 90 subset ["weakA_Bnum"]. The value of the candidate parameter for the amplitude of peak B 91 in the strong peak A 90 epochs is based on the average amplitude (e.g., amount of red) of peak B 91 in the epochs in the strong peak A 90 ["strongA_Bamp"] subset. The value of the candidate parameter for the amplitude of peak B 91 in the weak peak A 90 epochs are based on the average amplitude (e.g., amount of red) of peak B 91 in the epochs in the weak peak A 90 ["weakA_Bamp"] subset. In other embodiments, these candidate parameters measuring amplitude may be based on another factor other than average, such as median and generally, any measure of amplitude may be used.

Values for other similar candidate parameters may also be calculated for the reverse situation of subsets including peak B 91, with values based on peak A 90 amplitude or number ["strongB_Anum", "weakB_Anum", "strongB_Aamp", "weakB_Aamp"]. Further values for candidate parameters may also be calculated based on any permutation of a given subset of epochs (e.g., strong or weak) containing a peak (e.g., A, B, or C), and some measure of a quantity of the epochs in that subset (e.g., amplitude or count of another one of peak A 90, peak B 91, or peak C 92).

III.B.3. Other Candidate Parameters

The feature ratio area under the curve ["rAUC"] is calculated as the ratio of the area under the curve ("AUC") of peak C 92 to the AUC of peak A 90 from the averaged MEG data. The boundaries of peaks A and C are defined manually for each run, based on when each peak started and finished with respect to the horizontal baseline. Boundaries are straight vertical lines crossing the time chosen for the beginning and end of each peak. The area is then calculated by creating a straight baseline from the starting point of the boundary to the ending point of the boundary and summing the magnitude of the signal with respect to this baseline. Finally, the ratio between the two areas under the curves is calculated. In exemplary experiments, rAUC tended to be greater in normal test patients than cognitively-impaired test patients.

For the ratio latency ["rLat"], the latency of each peak from the averaged MEG data is determined by finding the time of the highest absolute magnitude of the signal within the three sets of pre-determined boundaries. Then, the difference between the latency of peak C 92 and latency of peak B 91 is calculated, and similarly, the difference between latency of peak B 91 and latency of peak A 90. The ratio of these differences is the value for rLat. In exemplary experiments, rLat tended to be lower for the cognitively-impaired test patients and was particularly low for one such test patients.

After an initial identification of the rAUC and rLat candidate parameters and investigation of their potential as model parameters, a more thorough identification and investigation was performed. As discussed previously, this included not just looking at averaged MEG data from numerous scans but also investigating the distribution of the activation over epochs in the heat maps of the model MEG data.

Other candidate parameters based on evaluating the heat maps included ["areaA_ratio"], which is the ratio of the area of peak A 90 in the weak peak A 90 epochs to the area of peak A 90 in the strong peak A 90 epochs; ["Bamp_ratio"], which is the ratio of the overall amplitude of peak B 91 in the stronger half of peak A 90 epochs to the overall amplitude of peak B 91 in the weaker half of peak A 90 epochs (a similar parameter can be determined and used for the C peaks ["Camp_ratio"], and similarly for any permutation of the peaks used to determine the weak and strong subsets, and the peak used to determine the ratio); ["Bnum sA/wA"], which is the ratio of the number of epochs having peak B 91 in the stronger half of peak A 90 epochs to the number of epochs having peak B 91 in the weaker half of peak A 90 epochs; ["Camp_ratio"], which is the ratio of the overall amplitude of peak C 92 in the stronger half of peak A 90 epochs to the overall amplitude of peak C 92 in the weaker half of peak A 90 epochs (a similar parameter can be used for the B peak ["Bamp_ratio"], and similarly for any permutation of the peaks used to determine the weak and strong subsets, and the peak used to determine the ratio); and ["Cnum sA/wA"], which is the ratio of the number of epochs having peak C 92 in the stronger half of peak A 90 epochs to the number of epochs having peak C 92 in the weaker half of peak A 90 epochs. Generally, further permutations of the above parameters are also possible. For example, any parameter including a ratio can also be calculated by inverting the values described above as making up the ratio.

Another candidate parameter, [badInPool], that can be added is a summation of how many candidate parameters in the pool were outside the range for normal test patients. For example, if the pool includes 17 candidate parameters, the value of [badInPool] is in the range of 0 to 17, depending on how many of the 17 candidate parameters a given AD test patient has a value outside the Gaussian distribution fitted to the normal test patient values. In other words, for each of the 17 candidate parameters, the normal values are gathered and fit to a Gaussian distribution. For each candidate parameter, if the value of the candidate parameter for an AD test patient has a probability of being in that distribution that is smaller than the smallest normal test patient probability, then a value of one is added to the [badInPool] candidate parameter. In other words, the less likely the excluded AD test patient was to be part of the normal distribution, the higher the value of the [badInPool] parameter.

To determine the [badInPool] candidate parameter, a separate calculation is made for each of the candidate parameters already in the ADD model. For a given candidate parameter, the MEG data for all normal test patients according to an already-determined cutoff for that model parameter (based on whether the MEG data comes from a normal test patient) is fit to a distribution, such as a normal (Gaussian) distribution. That distribution is used to estimate the smallest probability among normal test patients to be part of the normal test patients, where that value is used as a cutoff to mark the value of a given parameter as "bad" or not. In a leave-one-out cross-validation framework, the left-out patient is not used when estimating the normal distribution (although if the left-out patient were an AD patient, the value would not be used anyway).

The value of the [badInPool] candidate parameter for each patient is a simple summation of how many other candidate parameters for that test patient had smaller probabilities of being in the distribution for normal test patients than the smallest normal test patient probability. In an example ADD model having six other candidate parameters aside from [badInPool], [badInPool] can go from 0 to 6.

Another possible, similar candidate parameter is [weightInPool], which is a more detailed version of [badInPool]. The weight for [weightInPool] is a summation of the absolute differences between the smallest normal test patient probabilities and that test patient's corresponding probability of being in the distribution for normal test patients, summed over the set of candidate parameters in the model (other than [badInPool]). [badInPool] and [weightInPool] are both posthoc parameters.

III.C. Model Parameter Selection

Figure 3E:
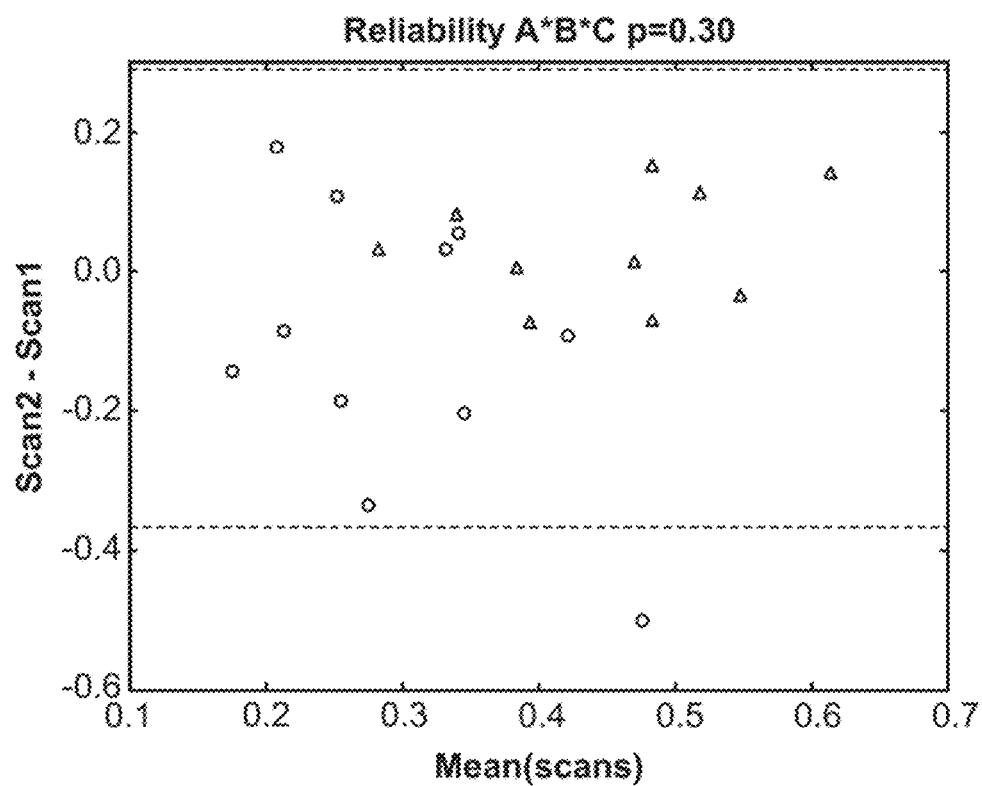
FIG. 3E shows an example Bland-Altman reliability plot for the candidate parameter A*B*C for an example set of test patients.
Figure 3F:
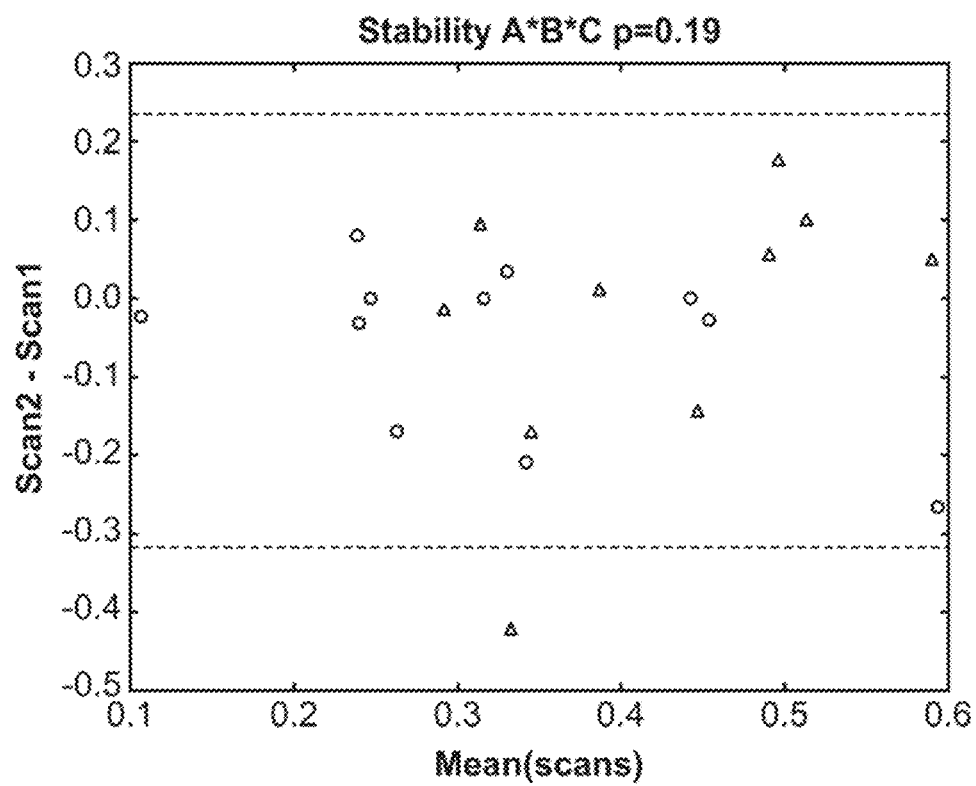
FIG. 3F shows an example Bland-Altman stability plot for the candidate parameter A*B*C for an example set of test patients.

The candidate parameters were evaluated based on whether they were reproducible within and across test patient visits (each visit generating a set of epochs) for reliability and stability, respectively. Bland-Altman plots were used to measure those characteristics. Two such plots appear in FIG. 3E and FIG. 3F, where the triangles are associated with MEG data from normal test patient and the circles are associated with MEG data from AD test patients. FIG. 3E shows a Bland-Altman plot of the reliability of the A*B*C candidate parameter. FIG. 3F shows an example Bland-Altman plot of the stability of the A*B*C candidate parameter for a set of test patients. In short, these plots compare the mean of two measurements and their standard deviation. The horizontal lines in FIG. 3E and FIG. 3F are 95% confidence interval lines, and any candidate parameter that had more than one patient outside the confidence boundaries for the reliability or the stability was deemed unsatisfactory.

In other embodiments, other criteria and methods may be used to evaluate the reliability and stability of candidate parameters, including, but not limited to, intraclass correlation coefficient ("ICC") and regression analysis.

Among the wide variety of possible candidate parameters that may be used to build the ADD model, thirty-seven candidate parameters were identified from visual analysis of MEG data to build one implementation of an ADD model. The subtle differences between the MEG scans of AD test patients and "normal" test patients described above were identified by careful manual visual review and observation and not by a computer algorithm. The 37 candidate parameters, previously described in Section III.B, include (as ordered from best to worst in terms of excluding AD test patients from the distribution for normal test patients) as weakA_Bamp, strongA_Bnum, nA, weakA_Camp, A*B*C, strongA_Bamp, B*C, areaC, duration (var), Cnum sA/wA, areaA, A*C, weakA_Cnum, nC, areaA_ratios, latencyA (var), onsetA (var), A*B, nB, offsetB (mean), strongA_Cnum, offsetB (var), Bnum sA/wA, Bamp_ratio, areaA/areaC, latencyB (mean), areaA/areaC, latencyB (var), offsetC (var), latencyA (mean), Camp_ratio, onsetA (mean), onsetB (mean), onsetB (var), duration (mean), strongA_Camp, and offsetC (mean).

Some of these candidate parameters were selected for further analysis based on being reliable and stable candidate parameters. Further analysis included determining the correlation between the candidate parameter and the MMSE score of the test patient 50. The selection of which reliable and stable candidate parameters became model parameters was based, at least in part, on the weights the linear and non-linear models assigned to the model parameters.

It is important to note that two participants with very similar MMSE scores were found to have very different peak C 92 amplitudes, which highlights how these candidate parameters may offer new insights into the disease that were hidden by just looking at MMSE scores.

III.D. Model Training

Once ADD model parameters are selected, the ADD model is trained to classify patients based on their MEG data. A wide variety of machine learning techniques can be used to create the ADD model, examples of which include Random Forest Classifiers ("RFC"), Random Classifier Regressors, Gradient Boosting, Support Vectors (also known as Support Vector Machine or "SVM"), Linear SVM, Radial basis function kernel SVM ("RBF SVM"), Linear Regression, Logistic Regression, and other forms of regressions. This list is not exhaustive, and one of skill in the art will appreciate that other machine learning techniques may also be used, including techniques in the field of deep learning such as Neural Networks.

Generally, training these models generates a set of coefficients, which may also be referred to as weights, that represent directly or indirectly how the values for the various model parameters correspond to either an MMSE score or a classification of a disease. In one implementation of any of the example models described in Section IV below, a set of model test patients were selected to include a subset having no known cognitive dysfunction and a subset showing a range of severity of symptoms of cognitive dysfunction, specifically cognitive dysfunction associated with AD. However, in practice the principles described herein may also be applicable to a variety of other diseases and conditions, including, but not limited to, mild cognitive disorder. In the case of an ADD example model generated using RFC with one-step classification, the coefficients may also be referred to as "critical values", as used in the literature regarding RFC models, in this case for categorizing the values of particular model parameters for a given patient as being normal or AD-indicative.

What the model is trained to detect may vary by implementation. Examples include a two-step classification and a one-step classification. In a two-step classification, a first model is used to predict the MMSE for a patient, and then a second model is used to categorize or quantify a patient with respect to a disease based on the predicted MMSE score. In a one-step classification, a single model categorizes or quantifies a patient with respect to the disease directly.

An advantage of the two-step approach is that there is value in the MMSE prediction, as the MMSE encodes several different aspects of human cognition, and is not inherently limited to the normal patient versus AD patient comparison. As such, other types of two step classifications can be used, determining MMSE score in a first step and then regressing to evaluate a different cognitive measure such as one of the other diseases listed above. A disadvantage of two step classification is that training an ADD model to determine an MMSE score requires an assessment of each test patient to obtain an MMSE score. In comparison, the one-step classification only needs a normal or AD label for training.

For two step classifications, the first step uses a linear/non-linear model, generally a linear or non-linear regression, although in alternate implementations more complicated algorithms may be used. After the MMSE score has been predicted, the second step includes using a simple cutoff to classify whether the test patient is a normal test patient or an AD test patient. For example, a set of predicted MMSE scores of test patients is fit to a linear model and one or more weights is determined that correlates the predicted MMSE scores with a categorization.

The ADD model may be a static model or a living model. In a static model, the model parameters and their weights are not changed as the model is used to evaluate and assess new patients. For example, in the RFC example, the normal value limits are calculated by fitting a Gaussian distribution to the set of normal patients minus whatever patient is left out in the cross validation. In a living model, new MEG data that has been collected from some or all new patients becomes additional model MEG data used to further train the weights of the candidate parameters or to add, delete, or change candidate parameters and thereby update the model. For a progressive disease, such as AD, the ADD model may also be fine-tuned by monitoring the patients and collecting model MEG data over time and re-evaluating the earlier ADD model MEG data, such as if a particular normal test patient begins to show symptoms of the progressive disease, to add, delete, or change candidate parameters and/or retrain the ADD model to re-determine the model weights, and thereby update the model.

IV. Examples

IV.A. Test Measurement Setup and Example Data Collection Protocol

An Elekta Neuromag® 306 channel MEG system 48 was used to record whole brain signals. The system had a total of 306 SQUID sensors 32, with each of the 102 locations having three different SQUID sensors 32: two planar gradiometer SQUID sensors 32 and one magnetometer SQUID sensor 32.

Figure 4A:
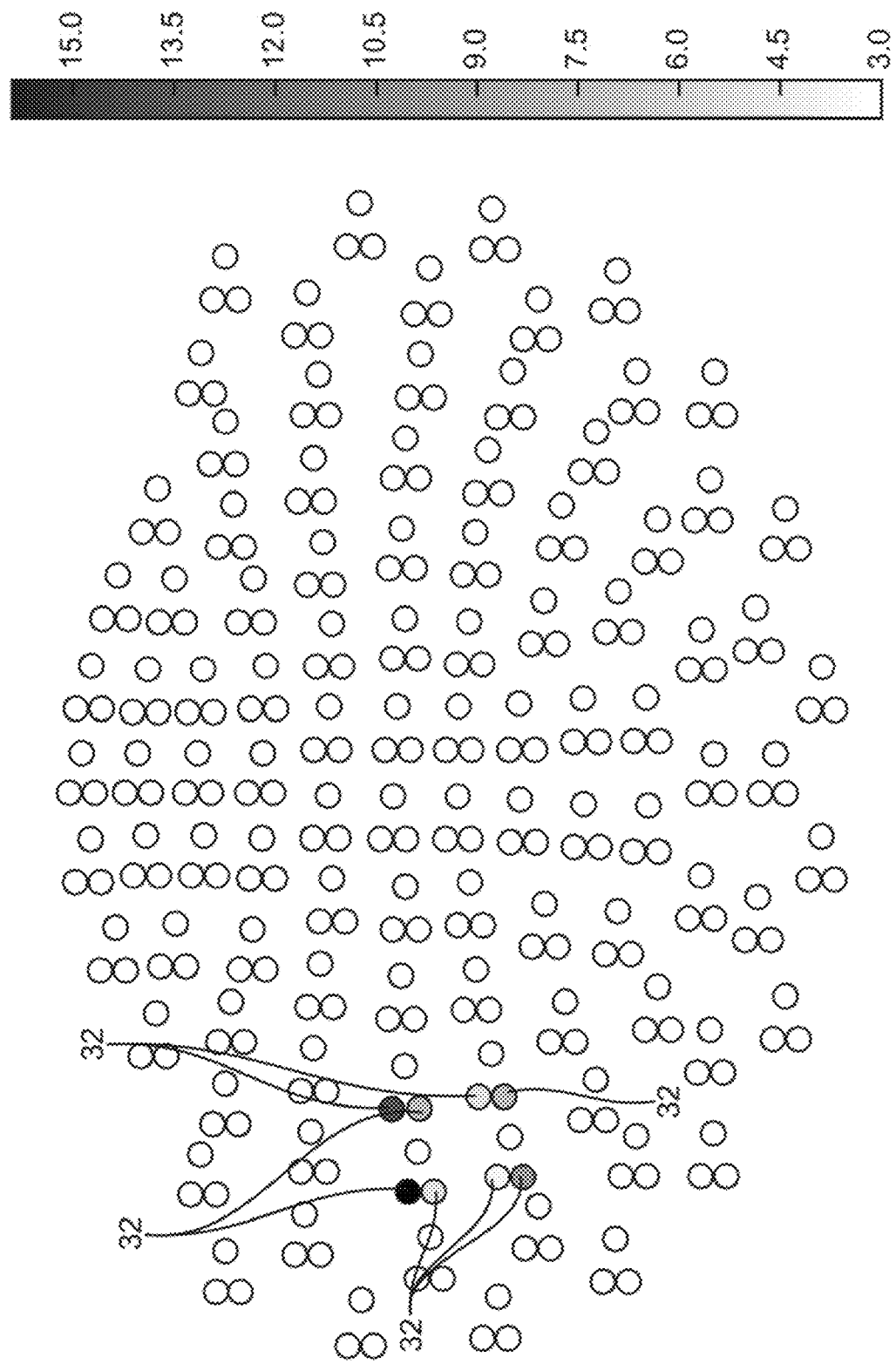
FIG. 4A shows schematically a gradiometer and magnetometer orientation of SQUID sensors in one embodiment.

FIG. 4A shows the array of SQUID sensors 32 for the Elekta Neuromag® MEG apparatus, with the shaded circles representing the generally most informative SQUID sensors 32, out of a pool of gradiometers located on the ipsilateral side of the helmet, for the ADD models described herein. Each circle in FIG. 4A represents a gradiometer or a magnetometer. As shown in FIG. 4A, the gradiometer SQUID sensors 32 are paired and are sensitive to magnetic fields that are at 90 degrees to each other. Also shown but not labeled in FIG. 4A, a magnetometer SQUID sensor 32 was associated with each pair of gradiometer SQUID sensors 32 in the MEG apparatus.

Gradiometer SQUID sensors 32 and magnetometer SQUID sensors 32 are structurally and functionally different from each other. Magnetometers measure the amplitude of the magnetic field (e.g. in Tesla units, T) at a certain point in space. Gradiometers measure the difference or gradient between magnetic fields (e.g. in Tesla/meter units, T/m) in two different points in space. These two points in space may be across the same spatial plane (e.g., a spatial gradiometer as in the Elekta system used herein), or along the same (Z) axis (e.g., an axial gradiometer).

The informative gradiometers used to generate the example models in this section tended to be at the eight locations of SQUID sensors 32 labeled in FIG. 4A, and only the data from these eight SQUID sensors 32 was used. These eight SQUID sensors 32 are most known for receiving signals from the left temporal region of the brain. These included sensors MEG0233, MEG0242, MEG0243, MEG1612, MEG1613, MEG1622, and MEG1623 of the Elekta Neuromag® 306 channel system. The colors in FIG. 4A represent the frequency of use in the ADD models described herein. There were a total of 63 sessions. The frequency of use from top to bottom of the four sensors in the left column was 16, 4, 3, and 9. The frequency of use from top to bottom of the four sensors in the right column was 13, 7, 4, and 7. This indicates that a much smaller SQUID sensor head 12 may be used if placed at the proper location on the head of the patient.

The experimental setup discussed above was used to capture the MEG data used to generate the models in this section. The specific details of the capture of the MEG data is discussed above in Section II, and is not repeated here for clarity and to condense this description.

The same set of test patients was used to build the example ADD models in this section. The set of test patients included twenty-one test patients, including ten normal test patients with no indication of cognitive impairment and eleven test patients who had already been diagnosed as having AD. An MRI was collected for each subject. Scans to record auditory evoked fields were run on the test patients in accordance with the setup and MEG data gathering steps discussed above. MEG recordings were performed in a magnetically-shielded room. All test patients except for one cognitively-impaired patient also received an MMSE score based on an administered MMSE test. Data from the test patient without an MMSE score was not used in the regression model but was used for the one-step classification tasks.

All of the test patients were white except for one black normal test patient and one black AD test patient. The normal test patient pool included five men and five women in an age range of 64 to 84 years, with a median age of 72 and a mean age of 73.9. The AD test patient pool included eight men and three women in an age range of 62 to 84 years, with a median age of 78 and a mean age of 76.2.

Figure 4B:
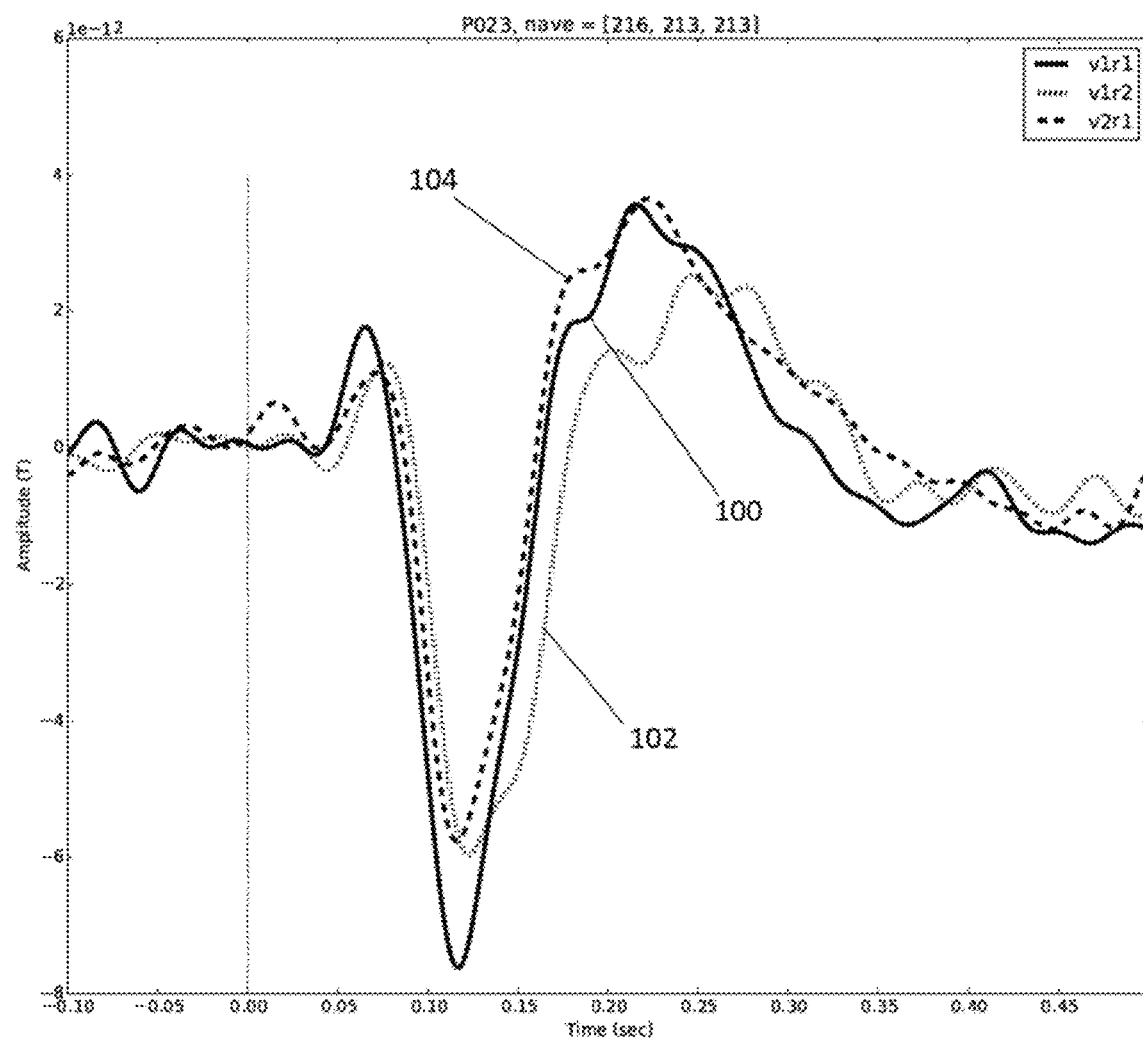
FIG. 4B shows example response signals from three different sessions on a representative normal patient.

FIG. 4B shows the three averaged response signal curves 100, 102, 104 from three example auditory stimulation test sessions, two done on the same day and the third being done on a different day, on a representative normal patient. These curves illustrate the general reproducibility between test runs for normal patients. However, they also highlight that there is a significant amount of non-uniformity between individual epochs even for normal patients, which the example ADD models described in this section are able to quantify and capture.

Figure 4C:
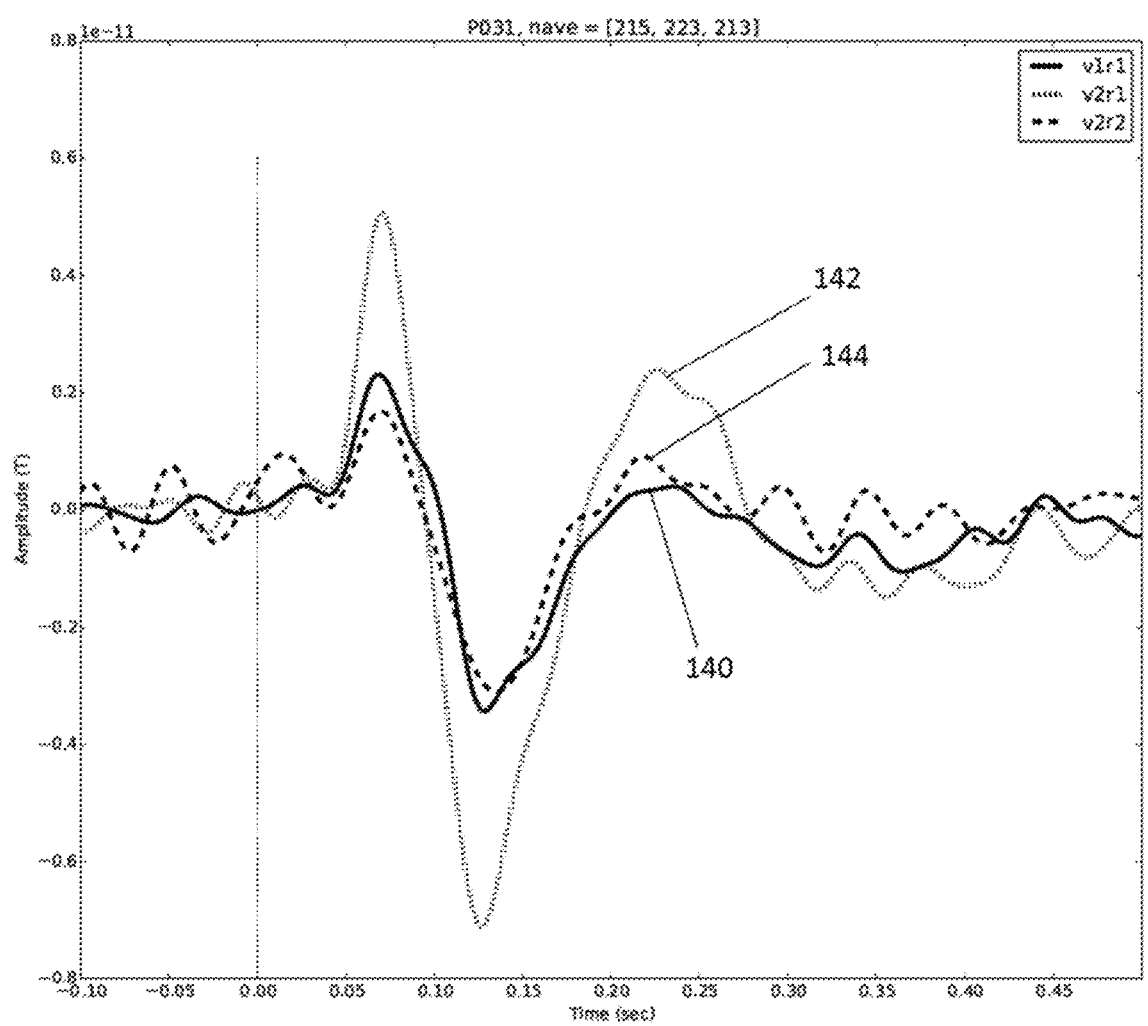
FIG. 4C shows example response signals from three different test sessions on an AD patient.

FIG. 4C shows the three averaged response signal curves 140, 142, 144 from three example auditory stimulation test sessions, two done on the same day and the third being done on a different day, on a representative AD patient. Although two of the curves are very similar, the peaks and valley of the third are significantly greater in magnitude. These curves illustrate the relative lack of reproducibility between test runs for AD patients. However, like the normal patient curves they also highlight that there is a significant amount of non-uniformity between individual epochs for AD patients as well, again which the example ADD models described in this section are able to quantify and capture.

The MEG data used to produce the averaged MEG data curves shown in FIG. 2A, FIG. 2B, FIG. 4B, and FIG. 4C may come from hundreds of repetitions of an evoked response from a single test session. Visualizing this MEG data in the form of a heat map, such as the one shown in FIG. 3A, allows visual inspection of the set of raw epoch data to identify trends and parameters that are hidden or lost in the averaged or otherwise collapsed MEG data. In such a heat map, each of the responses, or epochs, is plotted as a horizontal line with a color scale representing the strength of the measured magnetic field.

In developing the example model described in this section, gradiometer SQUID sensors 32 (i.e. only 204 out of the 306 SQUID sensors 32) were used, since those SQUID sensors 32 had the best power in discriminating between the two groups. These SQUID sensors 32 were selected on the basis of having minimum variability in peak A 92. For other models, however, the magnetometers (i.e. the other 102 out of the 306 SQUID sensors 32) may be used in place or in addition to the above-mentioned 204 SQUID sensors.

IV.B. Example Add Model 1

For a first example ADD model, a set of 17 candidate parameters that were both reliable and stable (see Section III.C.) were called "good" parameters, which were carried on for future analysis. Although many of the candidate parameters that failed the reliability and stability test were good at discriminating between normal and AD test patients, they were not selected for this particular ADD model as model parameters, because the candidate parameters were not sufficiently reproducible in other recording sessions of the same test patient.

From the good candidate parameters, normal distributions were established based on the mean and standard deviations of normal test patient values for each candidate parameter, and the number of AD test patients having probabilities lower than the lowest normal test patient of being part of the distribution was determined. In other words, the candidate parameter correctly sorted the AD test patient if the AD test patient's probability of being in the normal test patient distribution was smaller than the probability of the least likely normal test patient. The parameters were then scored based on how many ADs were outside the distribution for normal test patients (i.e., how many test patients were correctly marked as AD patients). That score (i.e. the number of AD test patients outside the distribution) was used as a preliminary rank of the good parameters.

The ranked set of 17 good candidate parameters were then selected to identify the candidate parameters that were included as model parameters in this ADD model. In this example embodiment, the candidate parameter that marked the most AD test patients correctly was selected first, added to the ADD model and considered the best model parameter. Each subsequent model parameter that was selected and added if it added the most information to that previous information (i.e. captured AD test patients not captured by previous candidate parameters). When two model parameters marked the same number of AD test patients (or same number of additional test patients), both were added together. This procedure was employed to minimize the number of candidate parameters used and therefore reduce the chances of overfitting. The model parameter selection continued until no more AD test patients were left to be marked.

This procedure selected the following six model parameters: the number of epochs with all three peaks 90, 91, 92 ["A*B*C"], the number of epochs with peak A 90 ["nA"], the amplitude of peak C 92 in the weak peak A 90 epochs ["weakA_Camp"], the amplitude of peak B 91 in the weak peak A 90 epochs ["weakA_Bamp"], the number of strong peak A 90 epochs with a peak B 91 ["strongA_Bnum"], and the variability of the duration of peak B 91 ["duration (var)"]. To this set of six candidate parameters, the [weightInPool] candidate parameter was also added. Thus, this example ADD model had seven model parameters in total.

The ADD model was then trained using a linear model on those seven parameters to predict MMSE score. A hard cutoff on predicted MMSE score was then used to classify the test patient as normal or AD. No cross validation was used, and thus the same data was used for both training and testing.

The result of the model was the predicted MMSE score, which was then split to classify the data. The model was able to perfectly distinguish between normal test patients and AD test patients based on predicted MMSE score.

IV.C. Example Add Model 2

Another ADD model was built using the same seven candidate parameters from the prior example ADD model (example ADD model 1) plus the posthoc [badInPool] candidate parameter for a total of eight model parameters.

Although very good correlation with MMSE score and group separation was shown in this model, each candidate parameter does not provide an answer in isolation. A very high correlation with MMSE score may be achieved, in one embodiment, by combining the best candidate parameters using a non-linear model (random classifier regressor) to predict MMSE scores, which are used to discriminate between normal test patients and AD test patients. This work makes it clear that while some test patients are marked as AD based on many candidate parameters, some others depend on characteristics of a smaller set of candidate parameters. This shows how a varied set of candidate parameters is effective at discriminating test patients. It further shows that candidate parameters derived from individual aspects of data from individual epochs are important in discriminating test patients, rather than, for example, entirely relying on data that aggregates, collapses or conflates MEG response data from multiple epochs together, such as by averaging data from multiple epochs.

IV.D. Alternative Modeling Technique Add Example Models

Different machine learning methods and model designs were tested using the full set or a subset of the 17 good candidate parameters described above. A summary of these results is shown in Table 1. For each of these model designs/method, both a two-step classification (regression to determine a hypothetical MMSE score, and then classification as AD or normal) and a simple classification as AD or normal between the two groups were tried. The hyperparameters for each machine learning method were left at default for each of these models. One of skill in the art will appreciate that tuning these hyper parameters will generally lead to improvement in the predictive power of these example ADD models.

Table 1 illustrates a number of example ADD models built using different sets of candidate parameters and trained using different machine learning techniques. As a key to the following table, "Two-step" and "One-step" denote whether two step classification or one step classification was used per the previous paragraphs. The example machine learning techniques used included Random Forest, Gradient Boosting, Support Vectors (also known as Support Vector Machine or "SVM"), Linear SVM, Radial basis function kernel SVM ("RBF SVM"), a Linear Regression, and a Logistic Regression. All example ADD models in Table 1 were trained using leave one out cross validation ("LOOCV").

The sets of model parameters used include "all" (all 17 good candidate parameters) with the [badInPool] and [weightInPool] parameters making 19 model parameters total, and all 17 good candidate parameters without the [badInPool] and [weightInPool] parameters making 17 model parameters, labeled in the table as "no InPool."

In Table 1, "r" denotes the correlation coefficient for all test patients and accuracy denotes the performance of the model in correctly categorizing the twenty test patients as normal or AD (e.g., 1 means all twenty test patients were categorizing correctly, etc.). For all of the two-step models, Pearson correlation coefficients (r) and p-value (p), as well as the Spearman correlation coefficient (r) and p-value (p), were calculated separately for both normal ("NV") and AD test patients. All such values in Table 1 are rounded to two decimal points.

TABLE 1

Machine Learning Method Results

| Method | r | Accuracy | NV Pearson | NV Spearman | AD Pearson | AD Spearman |
|---|---|---|---|---|---|---|
| Two-step Random Forest (all) | 0.8932 | 1.0 | r = 0.28 (p = 0.43) | r = −0.04 (p = 0.92) | r = 0.07 (p = 0.84) | r = 0.11 (p = 0.76) |
| Two-step Random Forest (no InPool) | 0.6685 | 0.75 | r = 0.77 (p = 0.01) | r = 0.71 (p = 0.02) | r = −0.34 (p = 0.33) | r = −0.40 (p = 0.26) |
| Two-step Gradient Boosting (all) | 0.9091 | 1.0 | r = −0.23 (p = 0.52) | r = −0.03 (p = 0.94) | r = 0.29 (p = 0.42) | r = 0.17 (p = 0.64) |
| Two-step Gradient Boosting (no InPool) | 0.3651 | 0.65 | r = 0.14 (p = 0.70) | r = 0.20 (p = 0.58) | r = −0.18 (p = 0.62) | r = −0.13 (p = 0.73) |
| Two-step Support Vectors (all) | 0.4435 | 0.5 | r = 0.29 (p = 0.41) | r = 0.40 (p = 0.25) | r = −0.34 (p = 0.33) | r = −0.24 (p = 0.50) |
| Two-step Support Vectors (no InPool) | 0.2582 | 0.5 | r = 0.17 (p = 0.64) | r = 0.18 (p = 0.63) | r = −0.37 (p = 0.30) | r = −0.33 (p = 0.35) |
| One-step Linear SVM (all) | | 0.9047 | | | | |
| One-step Linear SVM (no InPool) | | 0.8571 | | | | |
| One-step RBF SVM (all) | | 0.8571 | | | | |
| One-step RBF SVM (no InPool) | | 0.7143 | | | | |
| One-step Logistic Regression (all) | | 0.9524 | | | | |
| One-step Logistic Regression (no InPool) | | 0.8571 | | | | |

The results of these models illustrate several points. First, the two posthoc parameters, [badInPool] and [weightInPool] provide a substantial improvement to a model's performance. The ensemble non-linear models (RF and GBM) tend to outperform the others, given the current set of model parameters. High classification accuracies may also be obtained without taking the intermediate step of predicting MMSE scores. However, for reasons already stated herein, this is a highly useful characteristic of the models, for example, for use in evaluating for the presence or progression of other diseases.

IV.E. Example Add Models Based on Other Channel Selection Criteria

To evaluate the effect of the SQUID sensor 32 selection criterion, other selection criteria were tested. The tested criteria included selecting the SQUID sensor 32 that had the highest percentage of epochs having peak A 90 ("most peak A"), selecting the SQUID sensor 32 that had the highest percentage of epochs having peak B 91 ("most peak B"), and selecting the SQUID sensor 32 that had the highest intensity for peak A 90 ("highest peak A") using all epochs.

Once the sensor selection was made, the 37 candidate parameters were calculated based on the MEG data from those selected SQUID sensors 32, and the stability and reliability of each candidate parameter was evaluated independently to determine which candidate parameters were good. The most peak A 90, most peak B 91, and most intense peak A 90 sensor selection criteria produced 9, 17, and 11 good candidate parameters, respectively. Example ADD models were then developed using a two-step classification based on all of the good candidate parameters, and no InPool parameters. Again, RFC was used to predict MMSE scores and a regular cutoff on the predicted value was used to classify as normal or AD for the two-step classification. The results of this evaluation are shown in Table 2.

TABLE 2

ADD Model Results with Alternative Sensor Selection Criteria

| Sensor Criterion | r | Accuracy | NV Pearson | NV Spearman | AD Pearson | AD Spearman |
|---|---|---|---|---|---|---|
| Most peak A (all) | 0.3290 | 0.6 | r = 0.63 (p = 0.05) | r = 0.68 (p = 0.03) | r = −0.27 (p = 0.45) | r = −0.23 (p = 0.52) |
| Most peak A (no InPool) | −0.1564 | 0.45 | r = 0.34 (p = 0.34) | r = 0.29 (p = 0.42) | r = −0.10 (p = 0.79) | r = −0.09 (p = 0.82) |
| Most peak B (all) | 0.5614 | 0.65 | r = 0.26 (p = 0.47) | r = 0.37 (p = 0.30) | r = 0.35 (p = 0.32) | r = 0.23 (p = 0.53) |
| Most peak B (no InPool) | 0.2784 | 0.55 | r = 0.11 (p = 0.77) | r = 0.08 (p = 0.84) | r = 0.48 (p = 0.16) | r = 0.43 (p = 0.21) |
| Highest peak A intensity (all) | 0.6105 | 0.9 | r = 0.44 (p = 0.21) | r = 0.35 (p = 0.32) | r = −0.39 (p = 0.27) | r = −0.37 (p = 0.29) |
| Highest peak A intensity (no InPool) | 0.4665 | 0.6 | r = 0.35 (p = 0.32) | r = 0.42 (p = 0.23) | r = 0.40 (p = 0.25) | r = 0.39 (p = 0.27) |

Based on the test data presented herein, none of these alternative sensor criteria provided results as good as using the least variability in the latency of peak A 90 as the sensor selection criterion. However, it is clear that other alternative sensor criteria are still predictive and may be a viable substitute to minimizing peak A 90 latency variability. While there are many ways in which a single channel may be selected for use in extracting the features, the characteristic of peak A has yielded the best classifier results so far. That may be because of actual characteristics of peak A, or the number of stable and reliable features such selection scheme yields, compared to other methods.

IV.F. Additional Add Model Examples

In order to test how the number of model parameters affects the ADD model, a large number of additional example ADD models were created, where the number of good candidate parameters being used was varied for the Random Forest Regressor (RFR) ADD model in the leave-one-out cross validation framework described above in Section IV.E.3. Two-step classification was performed: as above, first predicting the MMSE score, second using the MMSE score to classify the patient between normal and AD. As above, the Random Forest Regressor uses its default parameters, and no hyperparameter optimization was performed. Two versions of each such ADD model were created, one with and one without the posthoc parameters ([badInPool] and [weightInPool]).

The number of ADD model parameter chosen at random from the pool of 17 good candidate parameters was fixed. Then, those model parameters were chosen randomly from the pool of good candidate parameters 200 different times, and histograms were created for the regression coefficient and accuracy. This produced 16 sets of histogram pairs (i.e., choosing one parameters at random, all the way to 17). Note that the variability of choosing one parameter at random (after 17 iterations), and 17 parameters (always the same ones, as there are only 17 parameters), comes from the Random Forest algorithm, which has a random component in splitting the trees.

Figure 4D:
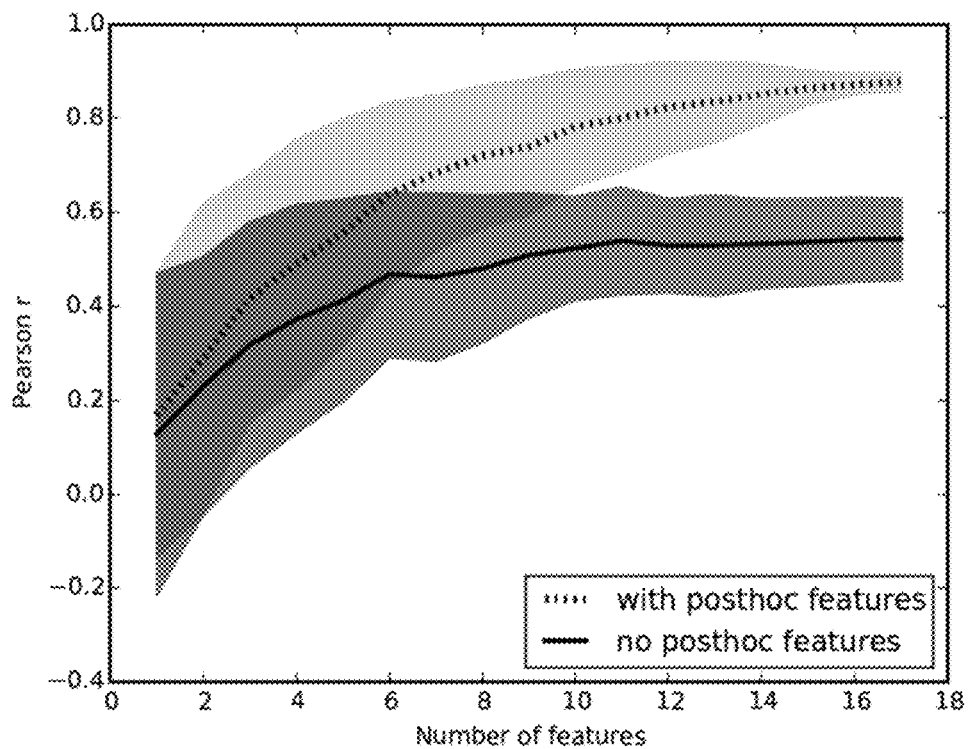
FIG. 4D shows the mean and standard deviation of the Pearson r value as a function of the number of candidate parameters used in an ADD model.

FIG. 4D shows the average and standard deviation for the Pearson r value (y-axis) as a function of the number of good candidate parameters (x-axis) included in the example ADD models both with and without posthoc parameters. In FIG. 4D, the average is illustrated as a solid line, and the standard deviation is illustrated as an envelope around that line.

Figure 4E:
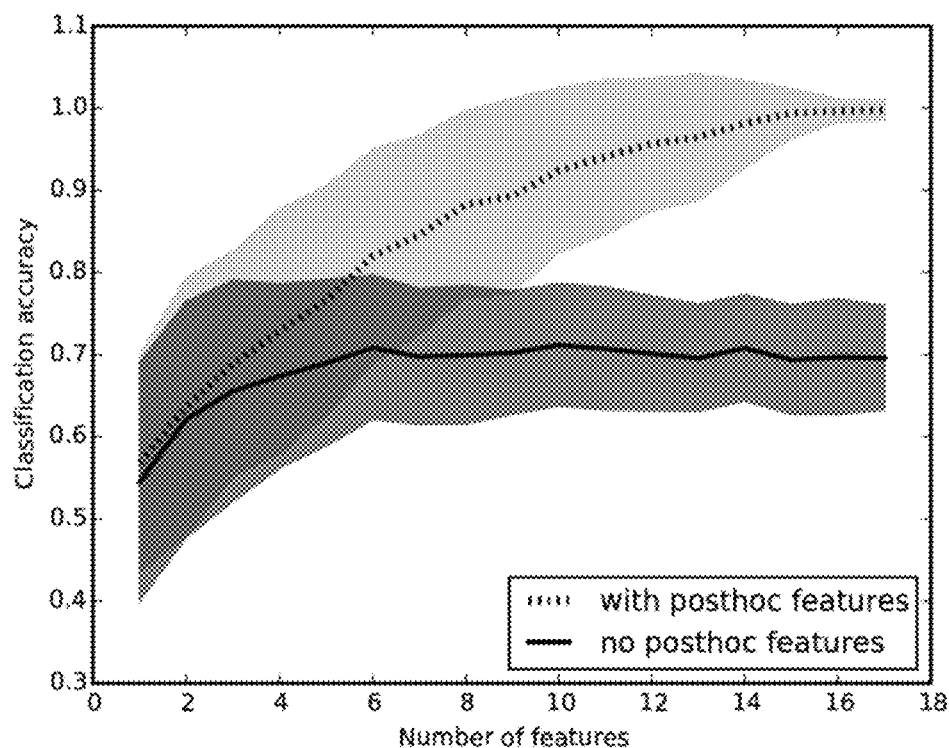
FIG. 4E shows the mean and standard deviation of the classification accuracy as a function of the number of candidate parameters used in an ADD model.

FIG. 4E shows the average and standard deviation for the classification accuracy as a function of the number of good candidate parameters included in the example ADD model both with and without posthoc parameters. FIG. 4E is otherwise illustrated similarly to FIG. 4D.

FIG. 4D and FIG. 4E show that the more of the good candidate parameters that are used, the better the performance of the resulting ADD model. They further illustrate that the two posthoc parameters are powerful. Further, the variance between posthoc and no posthoc parameters increases as the number of model parameters increases. Again, the deviation when all 17 good candidate parameters are used in the ADD model is a result of the randomization component of the Random Forest Regressor.

V. Model Use

A developed model, for example one of the ADD models mentioned above with a particular set of candidate parameters, may be applied to other "new" patients who were not part of the training set. The "new" MEG data is collected from the new patients in the same manner as the model MEG data was collected from the test patients. The new MEG data is then analyzed to determine the values of the model parameters for the model for the new patient. The values of the new patient's model parameters are compared to the model values for the model parameters, and an assessment of the new patient is provided. The assessment of the new patient relates to the medical condition that the model was developed to evaluate. The common example throughout this description is for discrimination of AD; however the processes throughout this description are applicable to other medical conditions.

The computer 20 calculates the model parameter values from the new patient MEG data, when possible, but human input may be helpful for the determination of some model parameter values, depending on the nature of the process to determine the model parameter value. After analysis of the new MEG data is complete, the results are provided.

FIG. 5 illustrates an example graphical user interface display that a doctor may use to quickly analyze the new patient after the collection of the MEG data. The upper left portion of the example display of FIG. 5 shows an example heat map of the new MEG data. The lower left portion of the example display of FIG. 5 shows curves of averaged MEG data for all epoch, strong peak A 90 epochs, and weak peak A 90 epochs, along with the estimates for the values of onsets and offsets. The upper right portion of the example display of FIG. 5 shows an example chart listing the model parameters of the model, the patient's values for those model parameters, and the normal values for those model parameters, along with highlighting of any abnormal results. The lower right portion of the example display of FIG. 5 shows an example chart that lists other candidate parameters, the patient's values for those candidate parameters, and normal values, and highlights any abnormal results. The example patient in FIG. 5 would be considered to have AD based on the information in FIG. 5.

Regarding the highlighting of abnormal parameters, the individual values for each model parameter contributing to the [badInPool] and [weightInPool] parameters as discussed above in Section III.B.3 can be used as part of a presented graphical user interface (GUI) display to determine which parameter values to highlight. Generally, when a given patient's value for a given model parameter is outside the range that is expected from a distribution of normal test patients, the value for that model parameter may be marked as abnormal in the GUI. For example, if, as above, the normal test patient values for all test subjects are used for model parameter A*B*C, and a distribution (e.g., a normal distribution) is estimated from that. Assume for this example that the smallest probability among normal test patients to be in that distribution is calculated as 0.2. Consequently any patient with probability <0.2 of being in the distribution for normal test patients will have the model parameter A*B*C marked in some distinguishing manner (e.g., in red as presented in FIG. 5).

Models that are trained based on the parameters to determine whether a patient is cognitively impaired can be used in methods of diagnosing cognitive impairment in a patient.

Models that are trained based on the parameters to determine whether a patient is cognitively impaired and to discriminate degrees of cognitive impairment can be used in methods of staging the extent of cognitive impairment in the patient. Such models can also be used in methods of monitoring progression of disease. In methods of monitoring disease progression, at least a first determination and a second determination of the degree of cognitive impairment are obtained at a spaced time interval, and the change in degree of cognitive impairment between first and second determinations is calculated.

Models that are trained based on the parameters to determine whether a patient is cognitively impaired and to discriminate cognitive impairment caused by neurodegeneration from cognitive impairment of other etiology can be used in methods of diagnostically discriminating cognitive impairment in a patient caused by neurodegeneration from cognitive impairment of other etiology.

The models can also be used in a method of treating a patient having cognitive impairment, the method comprising administering a therapeutically effective amount of an anti-cognitive impairment therapeutic agent to a patient who has been determined through use of the model to have cognitive impairment.

In some embodiments, the anti-cognitive impairment therapeutic agent is a disease-modifying anti-neurodegeneration agent. In some embodiments, the anti-cognitive impairment therapeutic agent is a cognitive symptom enhancement agent.

In certain embodiments, the disease-modifying anti-neurodegeneration agent binds to one or more of beta-secretase 1 (BACE-1), gamma secretase, Tau, Aβ, amyloid precursor protein (APP), α-synuclein, leucine rich repeat kinase 2 (LRRK2), parkin, presenilin 1, presenilin 2, apolipoprotein E4 (ApoE4), huntingtin, p75 neurotrophin receptor (p75NTR), CD20, prion protein (PrP), and death receptor 6 (DR6).

In specific embodiments, the anti-cognitive impairment therapeutic agent is selected from Table 3.

TABLE 3

| Agent (target or mechanism of action) | Company |
|---|---|
| ALKS 7119 (CNS modulator) | Alkermes |
| ALZ-801(amyloid beta-protein inhibitor) | Alzheon |
| ALZT OP1 (amyloid beta-protein inhibitor) | AZTherapies |
| ANAVEX ™ 2-73 | Anavex Life Sciences |
| ANAVEX ™ Plus (ANAVEX 2-73/donepezil) | Anavex Life Sciences |
| apabetalone (RVX-208) (BET protein inhibitor) | Resverlogix |
| ARC-029 (nilvadipine) | Archer Pharmaceuticals |
| ASP3662 (11-beta-HSD1 inhibitor) | Astellas Pharma US |
| AVN-101 (serotonin 6 receptor antagonist) | AllaChem & Avineuro Pharmaceuticals |
| AVN-322 (serotonin 6 receptor antagonist) | AllaChem & Avineuro Pharmaceuticals |
| AVP-786 (dextromethorphan)analogue/quinidine) | Avanir Pharmaceuticals & Concert Pharmaceuticals |
| AVP-923 (dextromethorphan/quinidine) | Avanir Pharmaceuticals |
| AXS-05 (bupropion/dextromethrophan) | Axsome Therapeutics |
| AZD3293 (BACE inhibitor) | AstraZeneca & Eli Lilly |
| azeliragon (TTP488) (RAGE antagonist) | vTv Therapeutics |
| BACE inhibitor | Eli Lilly |
| BAN2401 (humanized anti-amyloid beta mAb) | Biogen | Eisai |
| bexarotene (RXR-selective retinoid analogue) | ReXceptor |
| BI 409306 (phosphodiesterase 9A inhibitor) | Boehringer Ingelheim Pharmaceuticals |
| bisnorcymserine (butyrylcholinesterase inhibitor) | QR Pharma |
| BPN14770 (type 4 cyclic nucleotide phosphodiesterase inhibitor) | Tetra Discovery Partners |
| brexpiprazole (dopamine partial agonist) | Lundbeck & Otsuka Pharmaceutical |
| bryostatin 1 (protein kinase C stimulant) | Neurotrop BioScience |
| CAD106 (beta-amyloid protein inhibitor) | GlaxoSmithKline |
| CNP 520 (BACE1 protein inhibitor) | Amgen & Novartis Pharmaceuticals |
| CPC-201 (donepezil/peripherally acting cholinergic blocker fixed-combination)dose) | Chase Pharmaceuticals |
| CPC-212 (next-generation acetylcholinesterase inhibitor) | Chase Pharmaceuticals |
| crenezumab (beta-amyloid protein inhibitor) | Genentech |
| CSP-1103(amyloid beta-protein inhibitor) | CereSpir |
| donepezil transdermal patch | Corium International |
| E2027 | Eisai |
| E2609 (BACE1 protein inhibitor) | Biogen & Eisai |
| ELND005 (amyloid beta-protein inhibitor) | Transition Therapeutics |
| gantenerumab (amyloid beta-protein inhibitor) | Genentech |
| GC021109 (purinoceptor P2Y6 agonist) | GliaCure |
| GSK933776 (amyloid beta-protein inhibitor) | GlaxoSmithKline |
| idalopirdine (serotonin 6 receptor antagonist) | Lundbeck & Otsuka Pharmaceutical |
| immune globulin | Grifols USA |
| INP-102 intranasal | Impel NeuroPharma |
| JNJ-54861911 (BACE inhibitor) | Janssen Research & Development & Shionogi |
| LY3002813 (N3pG-amyloid beta mAb) | Eli Lilly |
| MEDI1814 (anti-amyloid beta mAb) | MedImmune |
| memantine transdermal patch | Corium International |
| MER 5101 (vaccine with beta-amyloid protein fragment) | MerciaPharma |
| MK-7622 (muscarinic M1 receptor modulator) | Merck |
| MSDC-0160(mTOT modulator) | Metabolic Solutions Development |
| NGP 555 (amyloid precursor protein secretase modulator) | NeuroGenetic Pharmaceuticals |
| NIC-515 (amyloid precursor protein secretase inhibitor) | Humanetics |

TABLE 3-continued

| Agent (target or mechanism of action) | Company |
| --- | --- |
| NTC-942 (serotonin 4 receptor agonist) | Nanotherapeutics |
| PF-05251749 | Pfizer |
| PF-06648671 | Pfizer |
| PF-06751979 | Pfizer |
| pioglitazone (insulin sensitizer) | Takeda Pharmaceuticals |
| piromelatine (melatonin agonist) | Neurin Pharmaceuticals |
| Posiphen ® (R-phenserine) | QR Pharma |
| rilapladib (Lp-PLA2 inhibitor) | GlaxoSmithKline |
| RVT-101 (serotonin 6 receptor antagonist) | Axovant Sciences |
| SAR228810 (anti-protofibrillar AB mAb) | Sanofi US |
| solanezumab (amyloid beta protein inhibitor) | Eli Lilly |
| SUVN-502 (serotonin 6 receptor antagonist) | Suven Life Sciences |
| SUVN-D4010 (serotonin 4 receptor agonist) | Suven Life Sciences |
| T-817MA (amyloid beta-protein inhibitor) | Toyama Chemical |
| T3D-959 (PPAR-delta/gamma agonist) | T3D Therapeutics |
| TGF-beta agonist | Stanford University & SRI Bioscience |
| TPI 287 (next-generation taxane) | Cortice Biosciences |
| TRx0237 (tau protein aggregation TDP-43 aggregation inhibitor)inhibitor/ | TauRx Pharmaceuticals |
| UB-311 (amyloid beta-protein inhibitor vaccine) | United Biomedical |
| verubecestat (MK-8931) (BACE1 protein inhibitor) | Merck |
| VX-745 (p38 mitogen-activated protein kinase inhibitor) | EIP Pharma |

Models that are trained based on the parameters to determine whether a patient is cognitively impaired and to discriminate degrees of cognitive impairment can also be used in methods of setting the dosage of an anti-cognitive impairment therapeutic agent in a patient having cognitive impairment. In typical embodiments, the method comprises determining the degree of cognitive impairment, and then setting the dosage of the anti-cognitive impairment therapeutic agent based on the determined degree of the patient's cognitive impairment.

Models that are trained based on the parameters to determine whether a patient is cognitively impaired and to discriminate degrees of cognitive impairment can also be used in methods of titrating the dosage of an anti-cognitive impairment therapeutic agent in a patient having cognitive impairment. In typical embodiments, a first determination and a second determination of the degree of cognitive impairment are determined at a spaced interval during which interval the patient has been receiving an anti-cognitive impairment therapeutic agent at a first dosage level, and the dosage is increased to a second dosage level if the degree of cognitive impairment has increased between the first and second determinations.

VI. Model Performance & Observations

Additional analysis may be done to evaluate the performance of a model once the model has been developed. To evaluate the example models described herein, the highest scoring good candidate parameters were used to predict the MMSE score of each test patient. Those calculations were performed using the entire dataset and also using cross-validation. In cross validation, one of the test patients is left out and the model is trained using all of the remaining test patients. The trained model is then used to predict the MMSE score of the left-out test patient. That evaluation was done for each test patient as the left-out test patient.

Figure 6A:
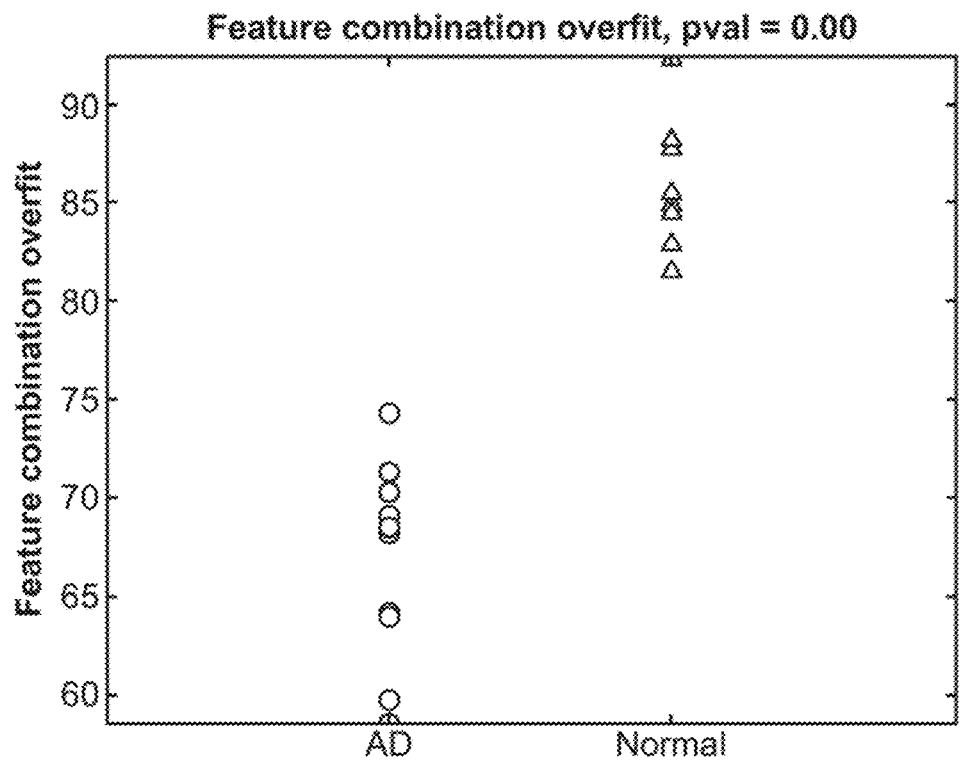
FIG. 6A shows separation of patients by patient group for a linear ADD model of seven model parameters.
Figure 6B:
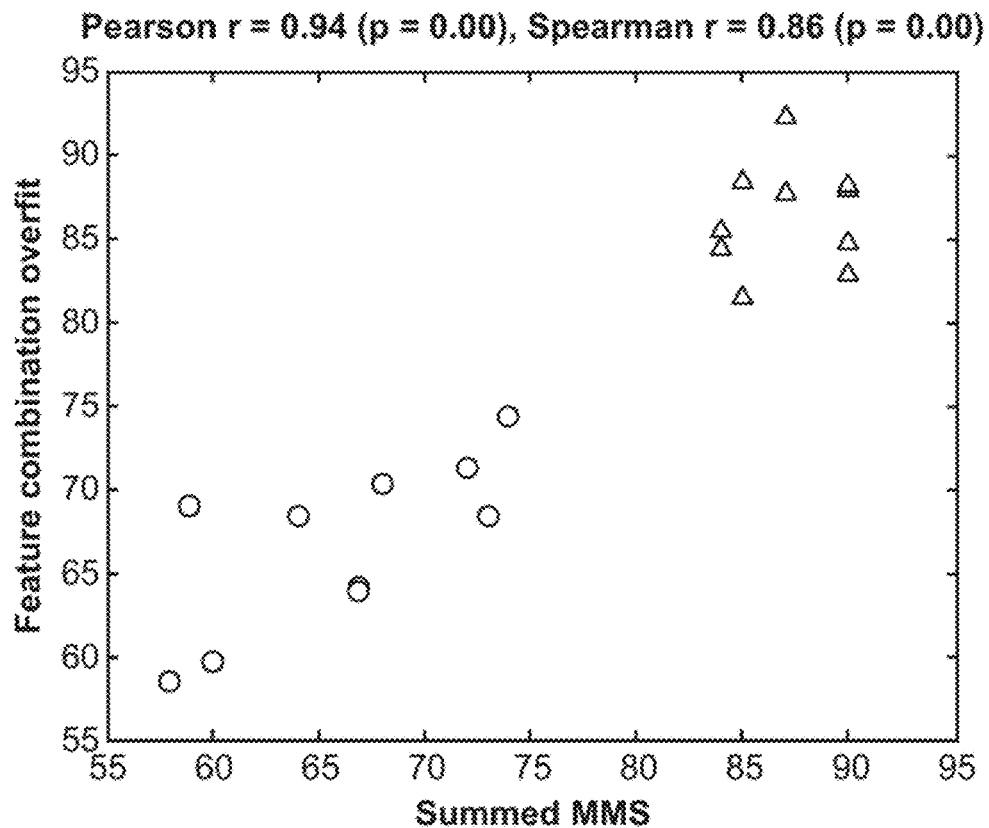
FIG. 6B shows separation of patients by summed Mini-Mental State Examination ("MMSE") score for the linear ADD model associated with FIG. 6A.
Figure 6C:
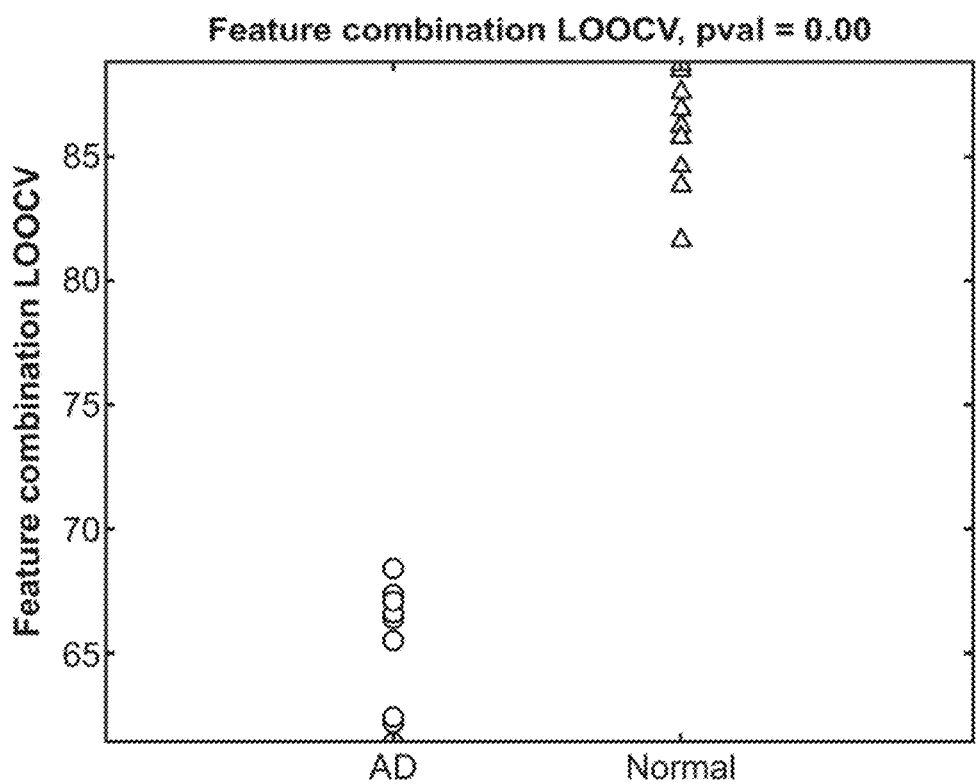
FIG. 6C shows separation of patients by patient group for a non-linear ADD model of eight model parameters.
Figure 6D:
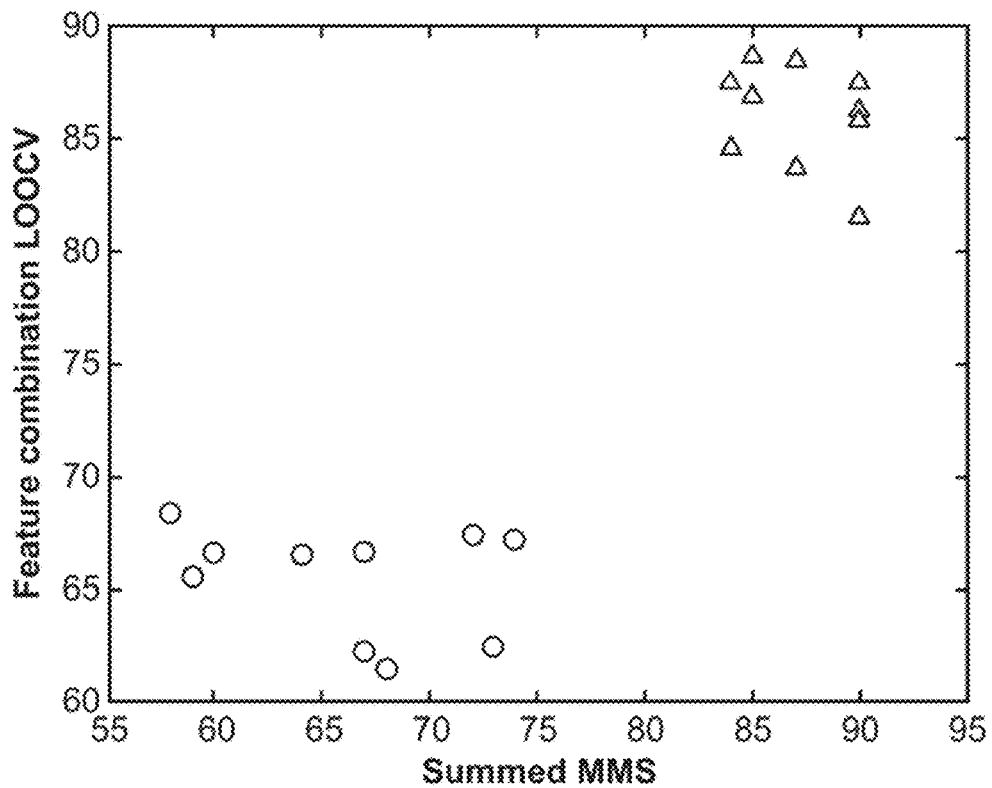
FIG. 6D shows separation of patients by summed MMSE score for the non-linear ADD model associated with FIG. 6C.

In the one-step classification model, the left-out test patient was classified directly as a normal test patient or an AD test patient, without predicting an MMSE score. In the two-step model, the left-out test patient was classified as a normal test patient or an AD test patient based on the predicted MIVISE score. Referring to FIG. 6A and FIG. 6B, the seven candidate parameter Example ADD Model 1, implemented as a linear model as described above without using LOOCV, provides a very good prediction of the MMSE score (r=0.94, p<0.001) for the left-out test patient. In this simulation of a clinical environment in which the status of the test patient is unknown, the model was able to perfectly discriminate between normal test patients and AD test patients. Referring to FIG. 6C and FIG. 6D, the eight candidate parameter Example ADD Model 2 using LOOCV, implemented as a non-linear model as described above, is still able to perfectly distinguish between normal and AD, but does not predict the MMSE score (r=0.88, p<0.001) as well as Example ADD Model 1. Specifically, a Random Forest Regressor was trained for the non-linear model using all good candidate parameters of the test patients and predicted the MMSE score of the left-out test patient. In other words, when using a leave-one-out cross validation with the non-linear model, the reliable and stable model parameters predict whether the left-out test patient was normal or AD with 100% accuracy (perfect sensitivity and specificity).

Although the model was developed using normal test patients and AD test patients, the model may allow for the identification of test patients with an intermediate level of cognitive function ("minimal cognitive impairment" or "MCI") between that of normal test patients and that of test patients with AD.

In the MEG data described herein, it appears that the peak A 90 is setting the "time lock" of the first note of the response for the peak B 91. The peak B 91 is then generated, with it being suspected that the peak B 91 is shared by signal connectivity with the frontal cortex and the peak C 92 then helps to characterize the peak B 91. A missing peak C 92 may be associated with a prolonged peak B 91 but is not a requirement for a correctly timed peak B 91.

The model may be used to detect temporal changes in a magnetic cortical surface map as a result of application of one or more controlled stimuli to a human patient as described herein. The results may be used to give a better understanding of the correlation between stimuli and human brain activity.

VII. Additional Considerations

Similar methodologies may be developed that may be useful in monitoring for other specific medical conditions or generally monitoring human brain function. The model described herein analyzes the MEG data collected after an auditory stimulus, including the relative extent of brain activation/excitation and subsequent response to the activation. The MEG data for the model may come from only a small number of the SQUID sensors generally from as few as a single SQUID sensor up to about six, although a full set of SQUID sensors (e.g., 306 sensors) may also be used.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A computer-implemented method, comprising:
accessing, by a processor, a set of epochs of magnetoencephalography (MEG) data of responses of a test patient to a plurality of auditory stimulus events;
determining, by the processor and for each epoch, a characteristic of a sorting peak in a tri-peak pattern, the tri-peak pattern comprising a first peak, a second peak, and a third peak, the sorting peak being one of the first peak, the second peak, or the third peak;
sorting, by the processor, the set of epochs based on values of the characteristic of the sorting peak of the epochs;
determining, by the processor, one or more parameters of the set of epochs that are sorted, each of the one or more parameters related to one or more of the first peak, the second peak, or the third peak; and
providing, by the processor and based on the one or more parameters, a determination whether the test patient is cognitively impaired.

2. The computer-implemented method of claim 1, wherein determining the characteristic of the sorting peak for at least one of the epochs comprises:
determining a timing window, and
determining an amplitude of a peak in the timing window as the characteristic.

3. The computer-implemented method of claim 1, further comprising:
transmitting data representing the set of epochs that are sorted as a visualization of a heat map for display.

4. The computer-implemented method of claim 1, further comprising:
determining an amplitude of the first peak, the second peak, or the third peak for each of the epochs based on the set of epochs that are sorted.

5. The computer-implemented method of claim 1, determining the characteristic of the sorting peak comprises:
assigning a normalized maximum value based on a maximum value of amplitude of the sorting peak for each of the epochs in the set.

6. The computer-implemented method of claim 1, wherein sorting the set of epochs comprises:
estimating initial peak boundaries for the set of epochs,
sorting the set of epochs based on the characteristic of the sorting peak defined by the initial peak boundaries, and
selecting a cutoff epoch for delineating between epochs that are determined to have and to not have the sorting peak.

7. The computer-implemented method of claim 1, wherein at least one of the parameters is a number of the first peak, the number of the second peak, or the number of the third peak presented in the set of epochs, and determining the at least one of the parameters comprises:
generating a real heat map that sorts the set of epochs based on the characteristic of the sorting peak, and
comparing the real heat map to a plurality of ideal heat maps, each ideal heat map associated with a candidate cutoff epoch,
determining spatial correlation between the real heat map and each of the ideal heat maps,
selecting, based on the spatial correlation, one of the ideal heat maps, and
using the candidate cutoff epoch of the selected ideal heat map to determine the at least one of the parameters.

8. The computer-implemented method of claim 1, wherein the MEG data is generated by a MEG device that comprises a plurality of sensors.

9. The computer-implemented method of claim 8, wherein the set of epochs of the MEG data is generated by one of the sensors, and selecting the one of the sensors is based on stability of the responses of the test patient to the plurality of auditory stimulus events.

10. The computer-implemented method of claim 8, wherein the set of epochs of the MEG data is generated by one of the sensors, and selecting the one of the sensors is based on reproducibility of a feature in the responses.

11. The computer-implemented method of claim 1, wherein the one or more parameters comprises one or more of the following: an amplitude, a count of peaks, an area under curve, an onset value, an offset value, a latency, a variability, or a duration.

12. The computer-implemented method of claim 1, wherein the first peak is a type-A peak, a type-B peak, or a type-C peak, and the second peak is a different one of those peaks.

13. The computer-implemented method of claim 1, wherein providing the determination whether the test patient is cognitively impaired comprises inputting the one or more parameters to a machine learning model that performs the determination.

14. The computer-implemented method of claim 13, wherein the machine learning model includes at least one of a random forest model, a gradient boosting model, a support vector machine (SVM) model, a linear SVM model, a radial basis function kernel SVM, a linear regression, a logistic regression, or a neural network.

15. A system comprising:
a magnetoencephalography (MEG) device configured to transmit a plurality of auditory stimulus events to a test patient and to measures responses of the test patient to generate at least a set of epochs of MEG data; and
a computing device that comprises one or more processors and memory configured to store instructions, the instructions, when executed by the one or more processors, cause the one or more processors to perform at least:

access the set of epochs of MEG data, determine, for each epoch, a characteristic of a sorting peak in a tri-peak pattern, the tri-peak pattern comprising a first peak, a second peak, and a third peak, the sorting peak being one of the first peak, the second peak, or the third peak, sort the set of epochs based on values of the characteristic of the sorting peak of the epochs, determine one or more parameters of the set of epochs that are sorted, each of the one or more parameters related to one or more of the first peak, the second peak, or the third peak, and provide, based on the one or more parameters, a determination whether the test patient is cognitively impaired.

16. The system of claim 15, wherein the instructions, when executed by the one or more processors, cause the one or more processors to further perform at least:

transmitting data representing the set of epochs that are sorted as a visualization of a heat map for display.

17. The system of claim 15, wherein the MEG device comprises a plurality of sensors.

18. The system of claim 17, wherein the set of epochs of the MEG data is generated by one of the sensors, and selecting the one of the sensors is based on stability of the responses of the test patient to the plurality of auditory stimulus events.

19. The system of claim 17, wherein the set of epochs of the MEG data is generated by one of the sensors, and selecting the one of the sensors is based on reproducibility of a feature in the responses.

20. A system comprising:

a computing device that comprises one or more processors and memory configured to store instructions, the instructions, when executed by the one or more processors, cause the one or more processors to perform at least:

access a set of epochs of magnetoencephalography (MEG) data of responses of a test patient to a plurality of auditory stimulus events, determine, for each epoch, a characteristic of a sorting peak in a tri-peak pattern, the tri-peak pattern comprising a first peak, a second peak, and a third peak, the sorting peak being one of the first peak, the second peak, or the third peak, sort the set of epochs based on values of the characteristic of the sorting peak of the epochs, determine one or more parameters of the set of epochs that are sorted, each of the one or more parameters related to one or more of the first peak, the second peak, or the third peak, and provide, based on the one or more parameters, a determination whether the test patient is cognitively impaired; and a user interface in communication with the computing device, the user interface configured to display the determination.

* * * * *